US011213308B2

(12) United States Patent
Altman et al.

(10) Patent No.: US 11,213,308 B2
(45) Date of Patent: Jan. 4, 2022

(54) PARANASAL SINUS MEDICAL DEVICE AND USES THEREOF

(71) Applicant: SINUSAFE MEDICAL LTD, Kiryat Ono (IL)

(72) Inventors: Nir Altman, Kfar Etsyon (IL); Avinoam Gemer, Kiryat Ono (IL); Danny Hadar, Kibbutz Eyal (IL)

(73) Assignee: SINUSAFE MEDICAL LTD, Kiryat Ono (IL)

( * ) Notice: Subject to any disclaimer, the term of this patent is extended or adjusted under 35 U.S.C. 154(b) by 324 days.

(21) Appl. No.: 15/541,634

(22) PCT Filed: Jan. 7, 2016

(86) PCT No.: PCT/IL2016/050022
§ 371 (c)(1),
(2) Date: Jul. 5, 2017

(87) PCT Pub. No.: WO2016/110854
PCT Pub. Date: Jul. 14, 2016

(65) Prior Publication Data
US 2018/0000499 A1    Jan. 4, 2018

Related U.S. Application Data

(60) Provisional application No. 62/100,926, filed on Jan. 8, 2015.

(51) Int. Cl.
*A61B 17/24*    (2006.01)
*A61B 17/32*    (2006.01)
(Continued)

(52) U.S. Cl.
CPC ........ *A61B 17/24* (2013.01); *A61B 17/32002* (2013.01); *A61B 17/3421* (2013.01);
(Continued)

(58) Field of Classification Search
CPC ................ A61B 17/24; A61B 17/3421; A61B 17/32002; A61B 2017/00331;
(Continued)

(56) References Cited

U.S. PATENT DOCUMENTS

| 400,589 | A | 4/1889 | Molesworth |
| 2,525,183 | A | 3/1947 | Robison |

(Continued)

FOREIGN PATENT DOCUMENTS

| CN | 102525703 | 4/2012 |
| CN | 102512271 | 6/2012 |

(Continued)

OTHER PUBLICATIONS

International Search Report of PCT/IL2016/050022 Completed Mar. 30, 2016; dated Mar. 30, 2016 4 Pages.
(Continued)

*Primary Examiner* — Diane D Yabut
*Assistant Examiner* — Christina C Lauer
(74) *Attorney, Agent, or Firm* — The Roy Gross Law Firm, LLC; Roy Gross

(57) ABSTRACT

The present disclosure generally relates to the field of medical devices for treatment and diagnosis of paranasal sinus conditions and methods of using same. There is disclosed a device having a hollow shaft configured to be inserted into a paranasal sinus through a natural opening thereof. The hollow shaft is shaped/configured to reach a treatment area within the paranasal sinus.

21 Claims, 15 Drawing Sheets

(51) Int. Cl.
*A61B 17/34* (2006.01)
*A61B 17/00* (2006.01)
*A61B 17/3207* (2006.01)

(52) U.S. Cl.
CPC ............... *A61B 2017/00331* (2013.01); *A61B 2017/00685* (2013.01); *A61B 2017/320004* (2013.01); *A61B 2017/320008* (2013.01); *A61B 2017/320012* (2013.01); *A61B 2017/320733* (2013.01); *A61B 2017/320766* (2013.01)

(58) Field of Classification Search
CPC ......... A61B 2017/00685; A61B 2017/320023; A61B 2017/320004; A61B 2017/320012; A61B 2017/320008
See application file for complete search history.

(56) References Cited

U.S. PATENT DOCUMENTS

| | | | |
|---|---|---|---|
| 5,087,265 | A | 2/1992 | Summers |
| 5,370,653 | A | 12/1994 | Cragg |
| 5,496,338 | A * | 3/1996 | Miyagi .......... A61B 17/320758 15/23 |
| 5,685,838 | A | 11/1997 | Peters et al. |
| 5,957,881 | A | 9/1999 | Peters et al. |
| 6,042,598 | A | 3/2000 | Tsugita et al. |
| 6,048,339 | A | 4/2000 | Zirps et al. |
| 6,090,118 | A | 7/2000 | McGuckin, Jr. |
| 6,174,280 | B1 | 1/2001 | Oneda et al. |
| 6,293,957 | B1 | 9/2001 | Peters et al. |
| 6,319,242 | B1 | 11/2001 | Patterson et al. |
| 6,375,634 | B1 | 4/2002 | Carroll |
| 6,471,679 | B1 | 10/2002 | Sue |
| 7,678,099 | B2 | 3/2010 | Ressemann et al. |
| 7,785,337 | B2 | 8/2010 | Adams et al. |
| 8,343,179 | B2 | 1/2013 | To et al. |
| 8,465,508 | B2 | 6/2013 | Tal |
| 8,597,203 | B2 | 12/2013 | Flatland et al. |
| 8,721,591 | B2 | 5/2014 | Chang et al. |
| 8,801,738 | B2 | 8/2014 | Yoon et al. |
| 2002/0133111 | A1 | 9/2002 | Shadduck |
| 2003/0191474 | A1 | 10/2003 | Cragg et al. |
| 2006/0004323 | A1* | 1/2006 | Chang .................. A61F 2/82 604/28 |
| 2007/0239109 | A1 | 10/2007 | Dereuil |
| 2007/0264342 | A1 | 11/2007 | Oliver et al. |
| 2008/0027423 | A1 | 1/2008 | Choi et al. |
| 2008/0097516 | A1 | 4/2008 | Chang et al. |
| 2008/0154250 | A1 | 6/2008 | Makower et al. |
| 2008/0275483 | A1 | 11/2008 | Makower et al. |
| 2008/0281156 | A1 | 11/2008 | Makower et al. |
| 2009/0258330 | A1 | 10/2009 | Huber et al. |
| 2010/0030113 | A1 | 2/2010 | Morriss et al. |
| 2010/0076476 | A1 | 3/2010 | To et al. |
| 2010/0204773 | A1 | 8/2010 | Elmaleh et al. |
| 2011/0160740 | A1* | 6/2011 | Makower ............... A61B 17/24 606/115 |
| 2011/0201996 | A1 | 8/2011 | Melder |
| 2011/0282251 | A1 | 11/2011 | Baker et al. |
| 2011/0288477 | A1 | 11/2011 | Ressemann et al. |
| 2013/0012869 | A1 | 1/2013 | Cha et al. |
| 2013/0023894 | A1 | 1/2013 | Saleh |
| 2013/0023895 | A1 | 1/2013 | Saleh |
| 2013/0046316 | A1 | 2/2013 | Sullivan et al. |
| 2013/0053824 | A1 | 2/2013 | Seiden et al. |
| 2013/0165873 | A1 | 6/2013 | Morriss et al. |
| 2013/0184574 | A1 | 7/2013 | Newhauser, Jr. et al. |
| 2013/0211321 | A1 | 8/2013 | Dubois et al. |
| 2013/0225937 | A1 | 8/2013 | Schaeffer et al. |
| 2013/0226070 | A1 | 8/2013 | Solem |
| 2013/0253387 | A1* | 9/2013 | Bonutti .................. A61B 17/24 601/46 |
| 2013/0282113 | A1 | 10/2013 | Punga et al. |
| 2013/0310734 | A1 | 11/2013 | Biel et al. |
| 2014/0012309 | A1 | 1/2014 | Keith et al. |
| 2014/0276626 | A1 | 9/2014 | Jenkins et al. |
| 2014/0276654 | A1 | 9/2014 | Jenkins |
| 2014/0277043 | A1* | 9/2014 | Jenkins ............... A61B 17/3205 606/170 |

FOREIGN PATENT DOCUMENTS

| | | |
|---|---|---|
| CN | 202505522 | 10/2012 |
| CN | 203001031 | 6/2013 |
| CN | 203139339 | 8/2013 |
| DE | 8900494 | 3/1989 |
| JP | 2001510068 A | 7/2001 |
| JP | 2007521916 A | 8/2007 |
| JP | 2009505691 A | 2/2009 |
| KR | 101179692 | 11/2011 |
| WO | 1982004388 | 12/1982 |
| WO | 9904701 | 2/1999 |
| WO | 2005077284 A2 | 8/2005 |
| WO | 2006015111 | 2/2006 |
| WO | 2007021433 | 2/2007 |
| WO | 2012052827 | 4/2012 |
| WO | 2014072977 | 5/2014 |
| WO | 2016110854 | 7/2016 |

OTHER PUBLICATIONS

Written Opinion of ISR of PCT/IL2016/050022 Completed Mar. 30, 2016; dated Mar. 30, 2016 6 Pages.

* cited by examiner

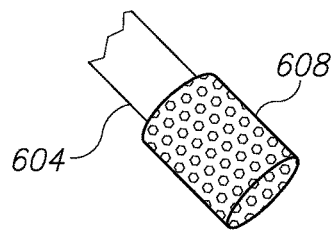
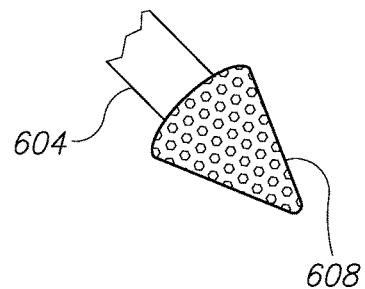
FIG.6A                FIG.6B
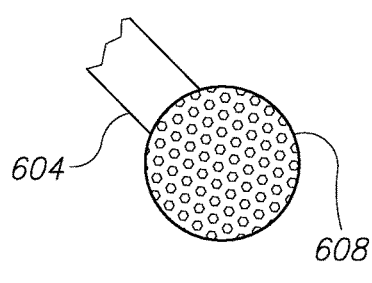
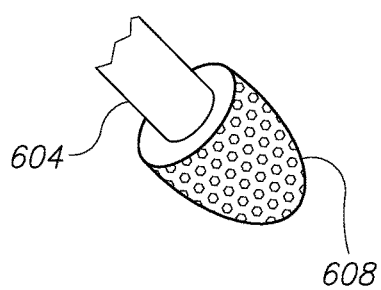
FIG.6C                FIG.6D
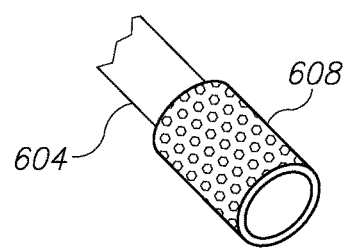
FIG.6E

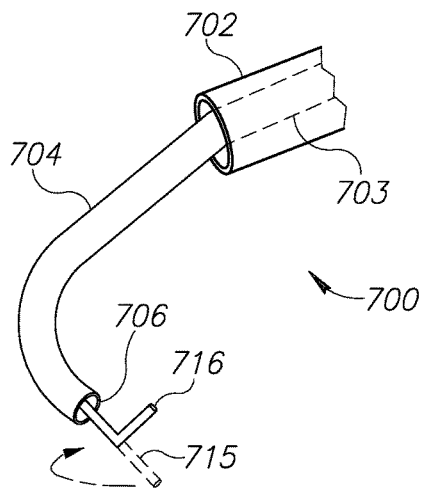
FIG.7A
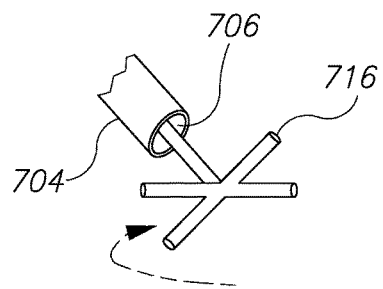
FIG.7B
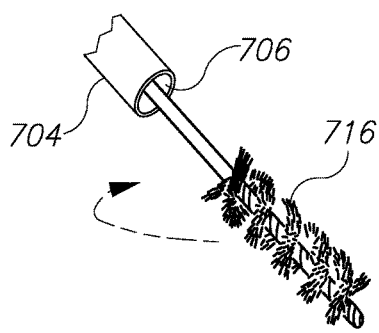
FIG.7C
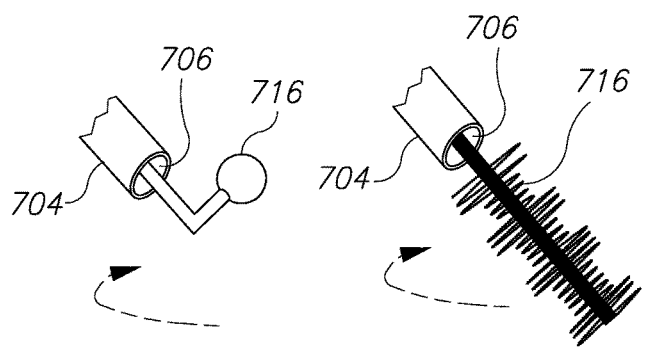
FIG.7D
FIG.7E
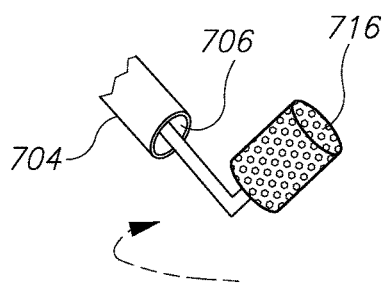
FIG.7F
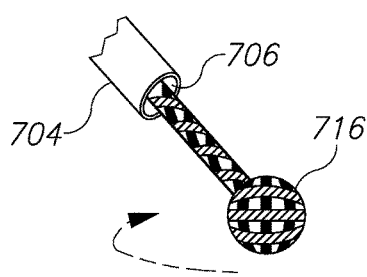
FIG.7G

PARANASAL SINUS MEDICAL DEVICE AND USES THEREOF

This application is a 35 U.S.C. § 371 national phase application of PCT/IL2016/050022, filed Jan. 7, 2016, which claims priority to U.S. 62/100,926 filed on Jan. 8, 2015. All applications are incorporated herein by reference as if fully set forth.

TECHNICAL FIELD

The present disclosure generally relates to the field of devices and methods for the treatment of paranasal sinus conditions.

BACKGROUND

Paranasal sinus conditions such as sinusitis, annually affects nearly 35 million patients in the United States alone. It can start with viral infections, allergy or autoimmune problems, and lead to persistent bacterial infections. The exact cause of sinusitis might be unclear to a health care provider as symptoms may be undistinguishable. Facing this uncertainty, the treatment of the condition is commonly carried out by administering various medications and/or providing various treatments thus determining the actual cause through a method of elimination of potential causes. As a result, the patient may be exposed to unnecessary drugs or procedures with their related risk and/or sequels. Moreover, in the last years, antibiotic resistant bacteria have become a major problem and traditional antibiotic treatments have become less effective for most sinusitis patients.

Another possibility is to surgically penetrate the paranasal sinus by puncturing through the paranasal sinus bones or by breaking the bones around the paranasal sinus natural opening for taking samples and determining the cause of the condition. Treatment can be administered during such surgery, for example by a process known as lavage or irrigation and aspiration. Many complications are associated with these surgical options; therefore, health providers tend to be reluctant in executing them unless necessity calls for it in acute cases.

There is thus a need in the art to provide devices, systems and methods allowing diagnosis and treatment of paranasal sinus conditions, without exposing the patient to unnecessary medication and/or massively invasive surgical intervention.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other advantages or improvements.

According to some embodiments, there are provided herein devices, systems and methods for treating and/or diagnosing paranasal sinus conditions using a hollow cannula, which may access the paranasal sinus through the natural paranasal sinus opening, thereby facilitating diagnosis and/or treatment of the paranasal sinus conditions without surgical dilation or expansion.

According to some embodiments, there is provided a medical device for treating and/or diagnosing a paranasal sinus condition, the medical device comprising a flexible hollow cannula configured to be at least partially inserted through an ostium into a sinus cavity of a subject, the flexible hollow cannula comprising a flexible grinding wire or spring, configured to grind, chop and/or stir material present in the sinus cavity and/or inside the hollow cannula. According to some embodiments, activation of the medical device induces precession of the flexible grinding wire and/or of the hollow cannula, thereby augmenting the grinding, chopping and/or stirring of the material.

According to some embodiments, there is provided a medical device for treating and/or diagnosing a paranasal sinus condition, the medical device comprising: a flexible hollow cannula configured to be at least partially inserted through an ostium into a sinus cavity of a subject, the flexible hollow cannula comprising a flexible grinding wire configured to rotate along a longitudinal axis thereof and thereby grind, chop and/or stir material present in the sinus cavity and/or inside the hollow cannula.

According to some embodiments, the device further includes an elongated tubular member configured to receive the flexible hollow cannula, wherein the elongated tubular member comprises a distal end being bent or bendable so as to face the ostium of the paranasal sinus, once inserted into the subject's nose.

According to some embodiments, there is provided a method for treating and/or diagnosing a paranasal sinus condition, the medical device comprising: inserting, at least partially, a flexible hollow cannula through an ostium into a sinus cavity of a subject, the flexible hollow cannula comprising a flexible grinding wire; and activating rotation of the grinding wire along a longitudinal axis thereof, thereby grinding, chopping and/or stirring material present in the sinus cavity and/or inside the hollow cannula. The method may further include conducting irrigation and/or aspiration during the rotation of the grinding wire.

According to some embodiments, there is provided a medical system for treating and/or diagnosing a paranasal sinus condition, the medical device comprising: a flexible hollow cannula configured to be at least partially inserted through an ostium into a sinus cavity of a subject, the flexible hollow cannula comprising a flexible grinding wire configured to rotate along a longitudinal axis thereof and thereby grind, chop and/or stir material present in the sinus cavity and/or inside the hollow cannula; an elongated tubular member configured to receive the flexible hollow cannula, wherein the elongated tubular member comprises a distal end being bent or bendable so as to face the ostium of the paranasal sinus, once inserted into the subject's nose; and a handle mechanically connected to the tubular member at a proximal end thereof, the handle is configured to control movement and extension of the hollow cannula, the handle comprises a pumping-orifice configured to provide fluid to the hollow cannula, and a suction-orifice configured to provide suction from the hollow cannula.

According to some embodiments, the precession of the hollow cannula may enlarge the ostium. According to some embodiments, the precession of the hollow cannula may reduce intra-sinus pressure.

According to some embodiments, the flexible grinding wire or spring is configured to grind sinus materials in the cannula and/or in the sinus during sinus irrigation and/or aspiration.

According to some embodiments, the grinding wire may be hollow. According to some embodiments, the grinding wire may be non-hollow.

According to some embodiments, the flexible grinding wire or spring is configured to propel sinus materials and irrigation liquids in the cannula and/or in the sinus, during sinus irrigation and/or aspiration, to facilitate irrigation and/or aspiration, to reduce aspirate viscosity, to reduce adhesive and friction forces, to force liquids into and in the cannula, to brake sinus material blocks or avoid cannula clogging. The effects may be performed directly by the grinding wire or spring and/or by the turbulence sheer forces created in the propelled irrigates and/or sinus materials.

According to some embodiments, the flexible grinding wire's rotation, vibration precession and/or back-and forth movement is configured to propel the sinus material and/or irrigates to the sinus ostium.

According to some embodiments, the sinus material may include but is not limited to, mucus, mucosa, bacteria, fungi, irrigation liquids or drugs.

According to some embodiments, the flexible hollow cannula is configured to retractably extend from the distal end of the elongated tubular member, and to penetrate through the ostium of the paranasal sinus, when the distal end of the elongated tubular member faces the ostium.

According to some embodiments, the flexible hollow cannula is configured to penetrate through the ostium without surgical dilation.

According to some embodiments, the external diameter of the flexible hollow cannula is smaller than the ostium. According to some embodiments, the external diameter is configured to allow fluids to flow out of the sinus via the ostium while the cannula is located within the ostium.

According to some embodiments, the medical device further comprises an actuator configured to extend and withdraw the flexible hollow cannula from and to the elongated tubular member.

According to some embodiments, the flexible grinding wire is configured to rotate along a longitudinal axis thereof.

According to some embodiments, the flexible grinding wire is configured to propel grinded material and/or irrigation fluids towards the sinus ostium.

According to some embodiments, the flexible grinding wire is configured to move back and forth along a longitudinal axis thereof.

According to some embodiments, the flexible grinding wire is configured to grind material within the flexible hollow cannula essentially along a length thereof.

According to some embodiments, the flexible grinding wire is configured to at least partially protrude out of the flexible hollow cannula.

According to some embodiments, the flexible grinding wire comprises a wire, a string, a fiber, a spring, a coil, a screw, a cable or any combination thereof. According to some embodiments, the flexible grinding wire has at least along a section of a length thereof a shape of a spring, a coil or a screw; the shape is configured to propel grinded material and/or irrigation fluids within the cannula towards a proximal end of the cannula and/or to reduce blockages within the cannula.

According to some embodiments, the flexible grinding wire is biodegradable.

According to some embodiments, the flexible hollow cannula and/or the flexible grinding wire comprise a super-elastic material. According to some embodiments, the super-elastic material is a pseudo-elastic material. According to some embodiments, the super-elastic material is a Nickel-Titanium alloy.

According to some embodiments, the flexible grinding wire is configured to assume a predetermined shape once delivered through the flexible hollow cannula and inserted into the sinus cavity.

According to some embodiments, the flexible grinding wire is configured to assume a predetermined shape comprising at least one curve at a distal end thereof.

According to some embodiments, the distal end of the flexible grinding wire is configured to assume a predetermined shape comprising a loop.

According to some embodiments, the flexible grinding wire comprises, at a distal end thereof, a knot and or knob to augment grinding.

According to some embodiments, the flexible grinding wire, once delivered through the flexible hollow cannula and inserted into the sinus cavity, is configured to assume a desired configuration and position by contacting the cavity inner walls.

According to some embodiments, the distal end of the flexible hollow cannula comprises an atraumatic tip. According to some embodiments, the atraumatic tip comprises a guide wire.

According to some embodiments, the atraumatic tip is softer and/or more flexible than the cannula. According to some embodiments, the atraumatic tip is collapsible.

According to some embodiments, the atraumatic tip is equal in diameter or wider than the cannula's distal end. According to other embodiments, the atraumatic tip is narrower than the cannula's distal end.

According to some embodiments, the atraumatic tip is detachable from the cannula's distal end. According to some embodiments, the atraumatic tip is configured to be detached by irrigation liquids flowing into the sinus. According to some embodiments, the atraumatic tip is dissolvable when exposed to or immersed in irrigation and/or sinus materials. According to some embodiments, the atraumatic tip is biodegradable and/or bio-absorbable.

According to some embodiments, the atraumatic tip might be retrieved into the cannula and out of it by a transmission mechanism such as a wire, a spring, a cable or flexible shaft. According to some embodiments, the retrieved atraumatic tip and transmission mechanism may be a ramrod or a scouring stick configured to allow longitudinal movement of the atraumatic tip along at least part of the cannula.

According to some embodiments, the longitudinal movement of the atraumatic tip may controllably seal off or open the distal end of the hollow cannula. According to some embodiments, the ramrod may be configured to facilitate suction, irrigation and/or aspiration of the sinus cavity and/or to force liquids out of and into the cannula, thereby preventing or reducing aspirate viscosity, preventing or reducing adhesive and friction forces, and/or avoiding clogging of the cannula. The effects may be performed directly by the ramrod and/or by the propelled irrigates and/or sinus materials.

According to some embodiments, the atraumatic tip comprises a lens, a light source such as LED light, a camera or any combination thereof.

According to some embodiments, the atraumatic tip and/or the cannula are smooth. According to some embodiments, the atraumatic tip and/or the cannula comprises lube or self-lubrication material, such as hydrophilic cover.

According to some embodiments, the side-wall of the flexible hollow cannula comprises an aperture in a distal end thereof. According to some embodiments, the flexible grinding wire is configured to exit the flexible hollow cannula through the aperture.

According to some embodiments, the flexible cannula is configured to assume a predetermined shape once inserted into the sinus cavity. According to some embodiments, the flexible cannula is configured to assume a predetermined shape comprising at least one curve at a distal end thereof.

According to some embodiments, the flexible hollow cannula is configured to change its position and/or configuration once inserted into the sinus cavity, thereby directing the flexible grinding wire to a treatment area. According to some embodiments, the flexible hollow cannula is configured to assume a predetermined configuration once inserted into the sinus cavity, thereby directing the flexible grinding wire to a treatment area. According to some embodiments, the flexible hollow cannula is configured to assume a predetermined configuration once inserted into the sinus cavity, and the flexible grinding wire is also configured to assume a predetermined shape once delivered through the flexible hollow cannula and inserted into the sinus cavity.

According to some embodiments, the treatment area is the floor of the sinus cavity. According to some embodiments, the treatment area is the sinus medial side. According to some embodiments, the treatment area is the sinus dorsal side. According to some embodiments, the treatment area is defined by thickened or pathologic mucosa. According to some embodiments, the treatment area is defined by the presence of fungi bacteria or photogenes. According to some embodiments, the treatment area is defined by its proximity to a potential anatomical risk such as a nerve, blood vessel, eye or weak bone. According to some embodiments, the treatment area is chosen by the device's user to avoid anatomic potential hazard. According to some embodiments, the user may request the patient to tilt his head, for example to place his head between the knees. It is understood that such position may ease on the suction of the sinus material and enable using a shorter cannula in that the treatment area moves closer to the ostium.

According to some embodiments, the flexible hollow cannula is steerable. According to some embodiments, the device comprises an actuator configured to steer the cannula and/or the grinding wire to a treatment area. According to some embodiments, the medical device further comprises a registration/navigation system configured to indicate a position of the flexible hollow cannula and/or flexible grinding wire in relation to the subject's anatomy or treatment area.

According to some embodiments, the movement (rotation, vibration, precession and/or back-and forth movement) of the flexible grinding wire within the cannula causes a rotation, vibration and/or precession of the cannula and thus propels sinus materials and irrigation liquids in the sinus, for example during sinus irrigation and/or aspiration. According to some embodiments, the rotation, vibration precession and/or back-and forth movement of the cannula may reduce aspirate viscosity, reduce adhesive and friction forces, force liquids into the cannula, and/or prevent clogging of the cannula. The effects may be performed directly by the grinding wire or spring and/or by the turbulence sheer forces created in the propelled irrigates and/or sinus materials. According to some embodiments, the cannula rotation, vibration precession and/or back-and forth movement propels the sinus material and/or irrigates to the sinus ostium.

According to some embodiments, the flexible hollow cannula's rotation, vibration precession and/or back-and forth movement is configured to allow fluid flow out of the sinus via the ostium, while the cannula is located within the ostium, thereby irrigating the sinus.

According to some embodiments, the rotation, vibration, precession and/or back-and forth movement of the cannula may enlarge the ostium once inserted therethrough. That is, without being bound by any theory, the rotation, vibration, precession and/or back-and forth movement of the cannula may induce a gentle pressure on the walls of the ostium, thereby causing fluids and mucus, absorbed therein, to be expelled, consequently enlarging the ostium. According to some embodiments, the rotation, vibration, precession and/or back-and forth movement of the cannula, and thus the degree of force applied to the ostium walls, may be controllable. According to some embodiments, the ostium may be enlarged while preserving the mucosa and or the bones of the sinus cavity. According to some embodiments, the enlargement of the ostium may be atraumatic. However, according to some alternative embodiments, the pressure may be increased to cause bone fractures. According to some embodiments, the enlargement of the ostium may be reversible or irreversible. Each possibility is a separate embodiment.

According to some embodiments the enlargement of the ostium may improve irrigation flow as well as the evacuation of irrigates out of the sinus, thereby shortening the duration of the procedure.

According to some embodiments the gentle ostia mucosal pressure is configured to prohibit or reduce pressure accumulation within the sinus by enabling air and liquids movement in and out of the sinus, for example during sinus irrigation and aspiration.

According to some embodiments, the rotation, vibration, precession and/or back-and forth movement of the grinding wire is configured only to remove sinus mucus while substantially preserving the sinus mucosa. According to some embodiments, the rotation, vibration, precession and/or back-and forth movement of the grinding wire is configured to remove sinus mucus and sinus pathogens, such as bacterial biofilm and fungi, while preserving most of the sinus mucosa. According to some embodiments, the rotation, vibration, precession and/or back-and forth movement of the grinding wire is configured to remove only the sinus mucosa, while leaving the sinus bone unharmed. According to some embodiments, the rotation, vibration, precession and/or back-and forth movement of the grinding wire is configured to remove only thickened and/or pathologic sinus mucosa while preserving healthy sinus mucosa.

According to some embodiments, the flexible grinding wire is configured to rotate at at least 100 RPM. According to some embodiments, the flexible grinding wire is configured to rotate at at least 1000 RPM. According to some embodiments, the flexible grinding wire is configured to rotate at at least 5000 RPM. According to some embodiments, the grinding wire may rotate in one direction, e.g. clockwise or anti-clockwise rotation. According to some embodiments, the direction of rotation may change during use. For example, the grinder may perform a predetermined amount of rotation in a clockwise direction followed by a predetermined direction in an anti-clockwise direction or vice versa. According to some embodiments, the predetermined number of rotation may be same or different for each direction. According to some embodiments, the direction of rotation may change at predetermined time intervals, for example every 20 second, every 1 minute or any other suitable time interval.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

FIG. 6a-FIG. 6e schematically illustrate a protruding portion of a hollow shaft with a penetration facilitation element having different shapes and structures, according to some embodiments;

FIG. 7a-FIG. 7g schematically illustrate a protruding portion of a hollow shaft with a grinder, according to some embodiments;

DETAILED DESCRIPTION

Figure 1:
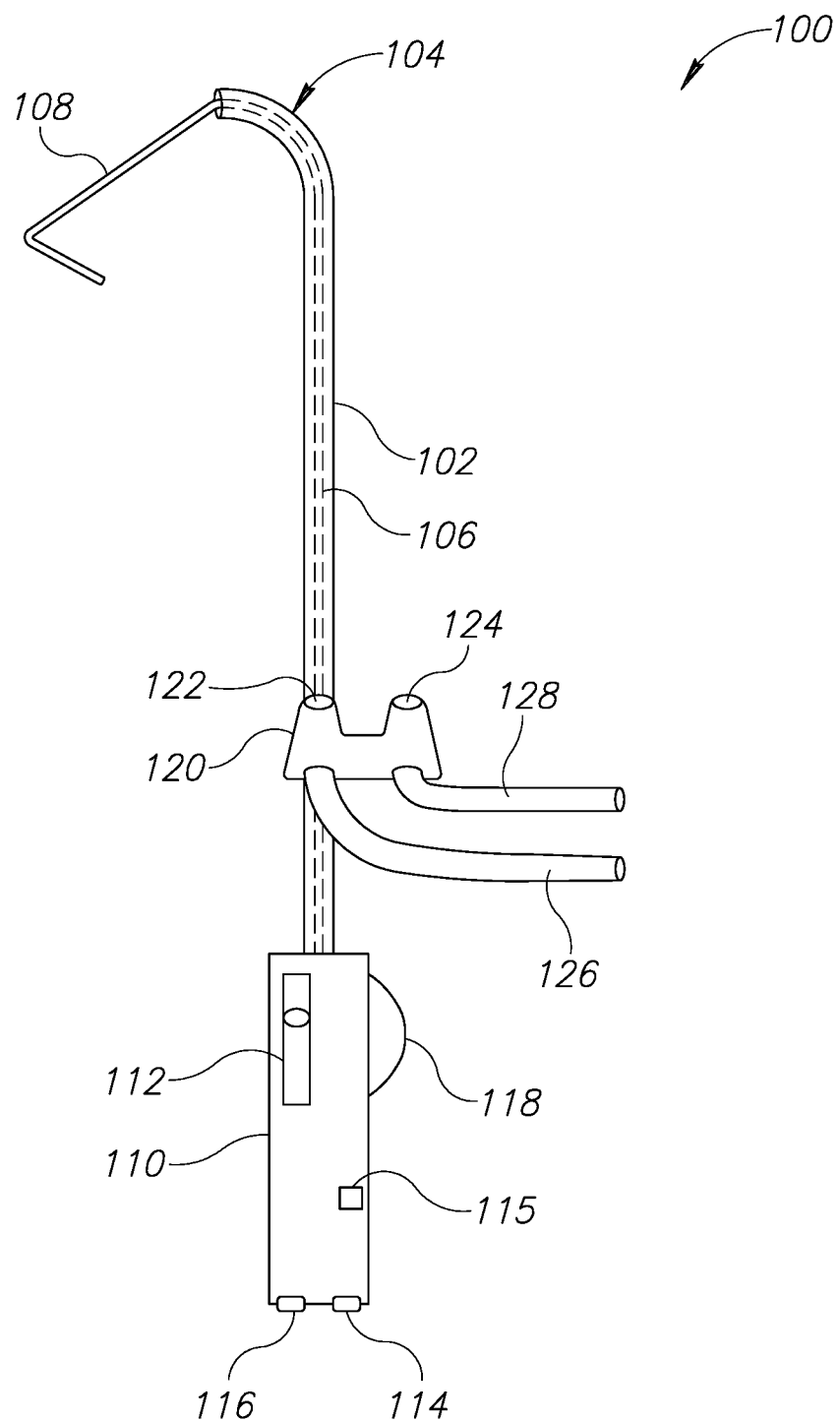
FIG. 1 schematically illustrates a device for treating a paranasal sinus condition, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

There is provided, according to some embodiments, a device for diagnosis and/or treatment of paranasal conditions including a hollow shaft (also referred to herein as a cannula) configured to be inserted into a paranasal sinus through a natural opening thereof. The hollow shaft has a relaxed shape configured to reach a desired treatment area within the paranasal sinus. The hollow shaft is movable and is at least partially located within a tubular member with a distal end configured to be inserted into a nasal cavity through a nostril, and to face a natural opening of a paranasal sinus.

In treatment and/or diagnosis, a healthcare provider may introduce the distal end of the tubular member to the nasal cavity of a subject. The tubular member may then be bent so as to face a natural opening of a paranasal sinus. A protruding portion or a hollow shaft may then be inserted through the natural opening to the paranasal sinus. According to some embodiments, when the protruding portion or the hollow shaft is extended, it obtains a relaxed shape that allows reaching a treatment area within the paranasal sinus.

Once the hollow shaft reaches the treatment area, a healthcare provider may extract samples for examination and diagnosis, perform irrigation and aspiration to the paranasal sinus, dissolve and/or remove mucus or tissue from within the sinus and/or administer pharmaceutical compositions/medications to the treatment area.

According to some embodiments, the insertion of the hollow shaft through the natural opening is minimally invasive and may entail no or minimal damage to the bones and tissues of the paranasal sinus and/or nasal cavity.

According to some embodiments, there is provided a medical device for treating and/or diagnosing a sinus condition. According to some embodiment, the sinus may be the paranasal sinus. As used herein, a "paranasal sinus" refers to an air-filled space that surrounds the nasal cavity. The paranasal sinuses include maxillary sinuses located under the eyes; the frontal sinuses above the eyes; the ethmoidal sinuses between the eyes; the sphenoidal sinuses behind the eyes. According to some embodiment, the sinus may be the mastoid sinus behind and the ostium may be the eustachian tube.

According to some embodiments, the medical device includes a flexible hollow cannula configured to be at least partially inserted through an ostium into a sinus cavity of a subject.

According to some embodiments, the flexible hollow cannula may be configured to penetrate through and/or be inserted into the ostium without requiring prior surgical dilation or expansion. That is, the flexible hollow cannula may be sized and shaped to enter the sinus through a natural sized opening thereof. According to some embodiments, the hollow cannula may have an external diameter of 2.5 mm or below, 2.0 mm or below, 1.5 mm or below, 1.2 mm or below or 1 mm or below. Each possibility is a separate embodiment.

According to some embodiments, the diameter of the flexible hollow cannula is smaller than the ostium so as to allow fluid flow out of the sinus via the ostium, while the cannula is located within the ostium, thereby enabling irrigation of the sinus. According to some embodiments, the flexible hollow cannula includes a grinding wire configured to grind, chop, propel, mix and/or stir mucus material.

As used herein the terms "mucus material" or "sinus material" or "mucosal material" or "grinded material" or "aspirated material" may refer to mucus, fungus, bacteria, biofilm, polyps, mucosal soft tissue, mucosa, pathologic mucosa such as tumor or hypertrophic mucosa, irrigation fluids, administered drugs or any other material or combination of materials present in the sinus cavity and/or within the hollow cannula.

According to some embodiments, the medical device may further include an elongated tubular member configured to receive the flexible hollow cannula. The elongated tubular member may include a distal end being bent or bendable so as to face the ostium of the paranasal sinus, once inserted into the subject's nose. According to some embodiments, the flexible hollow cannula is configured to retractably extend from the distal end of the elongated tubular member, and to penetrate through the ostium of the paranasal sinus, when the distal end of the elongated tubular member faces the ostium.

According to some embodiments, the hollow cannula and/or the grinding wire may include and/or be made from a flexible material, such that activation of the medical device induces precession of the grinding wire, thereby augmenting the grinding, chopping and/or stirring of the mucus material.

According to some embodiments, the flexible grinding wire may be configured to rotate along a longitudinal axis thereof. According to some embodiments, the flexible grinding wire may be configured to rotate at at least 100 RPM, at least 200 RPM, at least 500 RPM, at least 1000 RPM, at least 2000 RPM, at least 5000 RPM, at least 10,000 RPM, or at least 20,000 RPM. Each possibility is a separate embodiment.

According to some embodiments, the grinding wire may rotate in one direction, e.g. clockwise or anti-clockwise rotation. According to some embodiments, the direction of rotation may change during use. For example, the grinder may perform a predetermined amount of rotation in a clockwise direction followed by a predetermined direction in an anti-clockwise direction or vice versa. According to some embodiments, the predetermined number of rotation may be same or different for each direction. According to some embodiments, the direction of rotation may change at predetermined time intervals, for example every 20 second, every 1 minute or any other suitable time interval.

According to some embodiments, the rotation of the flexible grinding wire may induce precession of the flexible hollow cannula, thereby augmenting the stirring and/or grinding action of the flexible grinding wire. According to some embodiments, the flexible grinding wire may be configured to move back and forth along a longitudinal axis thereof. According to some embodiments, the flexible grinding wire may be configured to propel grinded material and/or irrigation fluids towards the sinus ostium. According to some embodiments, the flexible grinding wire may be configured to stir irrigation liquids and/or mucus materials thereby causing turbulence in the sinus cavity.

According to some embodiments, the flexible grinding wire is configured to grind sinus materials in the cannula and/or in the sinus during sinus irrigation and/or aspiration.

According to some embodiments, the grinding wire may be hollow. According to some embodiments, the hollow grinding wire may be configured for suction of the grinded material out of the sinus cavity. According to some embodiments, the grinding wire may be non-hollow. It is understood that the rotation, vibration, precession and/or back and forth movement of the grinding wire relative to the material reduces the friction of the material and thus its viscosity, thereby easing the suction out of the material.

According to some embodiments, the flexible grinding wire or spring is configured to propel sinus materials and irrigation liquids in the cannula and/or in the sinus, during sinus irrigation and/or aspiration, so as to facilitate irrigation and/or aspiration, reduce aspirate viscosity, reduce adhesive and friction forces, force liquids into and in the cannula, and/or avoid clogging of the cannula. The effects might be performed directly by the grinding wire or spring and/or by the turbulence sheer forces created in the propelled irrigates and/or sinus materials.

According to some embodiments, the rotation, vibration, precession and/or back-and forth movement of the flexible grinding wire is configured to propel the sinus material and/or irrigates toward the sinus ostium.

According to some embodiments, the flexible grinding wire may be configured to grind material within the flexible hollow cannula essentially along a length thereof. According to some embodiments, the flexible grinding wire may be configured to grind material within the flexible hollow cannula essentially along an entire length thereof.

According to some embodiments, the flexible grinding wire may be configured to cause cavitation in the liquids and/or material present in the sinus cavity. According to some embodiments, the flexible grinding wire may exert a sheer force on material present in the sinus cavity.

According to some embodiments, the flexible grinding wire may be configured to at least partially protrude out of the flexible hollow cannula. Accordingly, at least part of the grinding may be performed outside the hollow cannula.

According to some embodiments, the flexible grinding wire may have an external diameter of 1.5 mm or below, 1.0 mm or below, 0.5 mm or below, 0.3 mm or below, 0.24 mm, 0.2 mm or below or 0.1 mm or below. Each possibility is a separate embodiment.

According to some embodiments, the flexible grinding wire may include a wire, a string, a fiber, a spring, a coil, a screw, a cable or any combination thereof. Each possibility is a separate embodiment. According to some embodiments, the flexible grinding wire may, at least along a section of a length thereof, have a shape of a spring, a coil or a screw. The shape may be configured to propel grinded material and/or irrigation fluids towards a proximal end of the cannula and/or to reduce blockages within the cannula. According to some embodiments, the grinding wire may be configured to prevent, loosen and/or remove mucus material accumulating and/or clogging the hollow cannula. According to some embodiments, the grinding wire may be configured to scrape, loosen and/or remove material sticking to the walls of the sinus cavity.

According to some embodiments, the grinding wire and/or the hollow cannula may be configured to collapse, to reduce its speed of rotation, vibration, precession and/or back-and forth movement and/or to deactivate the medical device if the walls of the sinus cavity are hit upon.

According to some embodiments, the rotation, vibration, precession and/or back-and forth movement of the grinding wire (optionally in conjunction with irrigation liquids administered) is configured only to remove sinus mucus while preserving most of the sinus mucosa. According to some embodiments, the rotation, vibration, precession and/or back-and forth movement of the grinding wire is configured to remove sinus mucus and sinus pathogens such as bacterial biofilm and fungi, while substantially preserving the sinus mucosa. According to some embodiments, the rotation, vibration, precession and/or back-and forth movement of the grinding wire is configured only to remove the sinus mucosa and to be harmless to the sinus bone. According to some embodiments, the rotation, vibration, precession and/or back-and forth movement of the grinding wire is configured to remove only the thickened or pathologic sinus mucosa and preserve healthy sinus mucosa.

According to some embodiments, the flexible grinding wire may be biodegradable. According to some embodiments, the flexible hollow cannula and/or the flexible grinding wire may include a super-elastic material. According to some embodiments, the super-elastic material may be a pseudo-elastic material. According to some embodiments, the super-elastic material may be a Nickel-Titanium alloy.

According to some embodiments, the flexible grinding wire may be configured to assume a predetermined two-dimensional or three-dimensional shape once delivered through the flexible hollow cannula and/or inserted into the sinus cavity.

According to some embodiments, the flexible grinding wire may be configured to assume a shape including at least one curve, at least one kink, at least one loop, at least one knot and/or knob, at least one element configured to increase the weight of the flexible grinding wire or any combination thereof. Each possibility is a separate embodiment. According to some embodiment, the at least one curve, the at least one kink, the at least one loop, the at least one knot and/or knob, the at least one element configured to increase the weight of the flexible grinding wire or combination thereof may augment the grinding effect of the flexible grinding wire. According to some embodiments, the at least one curve, the at least one kink, the at least one loop, the at least one knot and/or knob, the at least one element configured to increase the weight of the flexible grinding wire or combination thereof may be located at a distal end of the flexible grinding wire.

According to some embodiments, the flexible grinding wire, once delivered through the flexible hollow cannula and inserted into the sinus cavity, may be configured to assume a desired configuration and position by contacting inner walls of the cavity. According to some embodiments, the desired configuration may include a bent relaxed shape such as, but not limited to, an arc shape or an L shape. Each possibility is a separate embodiment.

According to some embodiments, the flexible hollow cannula may be configured to change its position and/or configuration once inserted into the sinus cavity, thereby directing the flexible grinding wire to a treatment area. According to some embodiments, the flexible hollow cannula may be configured to assume a predetermined configuration once inserted into the sinus cavity, thereby directing the flexible grinding wire to a treatment area. According to some embodiments, the flexible hollow cannula may be configured to assume a predetermined configuration once inserted into the sinus cavity, and the flexible grinding wire may also be configured to assume a predetermined shape once delivered through the flexible hollow cannula and inserted into the sinus cavity.

According to some embodiments, the flexible hollow cannula may be configured to vibrate or rotate along a longitudinal axis thereof. According to some embodiments, the rotation, vibration and/or precession of the flexible hollow cannula may enable scraping off material accumulated on the walls of the sinus cavity. According to some embodiments, the rotation, vibration and/or precession of the flexible hollow cannula may stir and/or induce turbulence of liquids present in the sinus cavity. According to some embodiments, the flexible grinding wire may be configured to cause cavitation in the liquids and/or material present in the sinus cavity. According to some embodiments, the flexible grinding wire may exert a sheer force on material present in the sinus cavity.

According to some embodiments, the rotation, vibration and/or precession of the flexible hollow cannula may be configured to augment the precession of the flexible grinding wire.

According to some embodiments, the flexible hollow cannula may include a compartment at a distal end thereof. According to some embodiments, the compartment may be configured to protect the surrounding walls of the cavity from being grinded by the flexible grinding wire. According to some embodiments, the compartment may be cone-shaped so as to accommodate the shape of the sinus cavity, so as to direct grinded material towards the sinus ostium during operation and/or so as to protect the walls of the sinus cavity from damage caused by the grinding wire.

According to some embodiments, the distal end of the cannula may be curved relative to the cannula's proximal end. According to some embodiments, the curve may be L-shaped or arc-shaped. According to some embodiments, the distal end of the cannula may be curved 10, 15, 20, 25, 30 degrees, relative to its proximal end. Each possibility is a separate embodiment. According to some embodiments, the angle of the cannula's distal end, relative to the elongated tubular member's proximal end, may be smaller or equal to 75, 80, 85, 90, 95, 100, 105 degrees (for example when used for the maxillary sinus). Each possibility is a separate embodiment. According to some embodiments, the angle of the cannula's distal end, relative to the elongated tubular member's proximal end, may be smaller than or equal to 45, 50, 55, 60, 65, 70, 75 degrees (for example when used for the frontal sinus). Each possibility is a separate embodiment. According to some embodiments, the angle of the cannula's distal end, relative to the elongated tubular member's proximal end, may be smaller than or equal to 0, 5, 10, 15, 20, 25, 30 degrees (for example when used for the sphenoid sinus). Each possibility is a separate embodiment.

According to some embodiments, the distal end of the flexible hollow cannula includes or forms an atraumatic tip. It is understood that the atraumatic tip may enable insertion of the hollow cannula through the ostium, while causing minimal discomfort to the patient. According to some embodiments, the atraumatic tip may include a guide wire, a lens, a light source, such as but not limited to a LED, a camera or any combination thereof. Each possibility is a separate embodiment.

According to some embodiments, the flexible hollow cannula includes an aperture in its side wall at a distal end thereof, such that the flexible grinding wire may exit the flexible hollow cannula through the aperture. It is understood that such configuration may enable sealing of the distal end of the hollow cannula with an atraumatic tip. It is further understood that by exiting the hollow cannula through the aperture, the grinding wire may be directed away from sensitive areas which it could potentially cause harm. As a non-limiting example, the aperture in the hollow cannula may be configured to ensure that the flexible grinding wire exits the hollow cannula as far away as possible from the eye when inserted into a maxillary sinus cavity.

According to some embodiments, the movement (rotation, vibration, precession and/or back-and forth movement) of the flexible grinding wire within the cannula may cause a rotation, vibration and/or precession of the cannula and thus propel sinus materials and irrigation liquids in the sinus, for example during sinus irrigation and/or aspiration. According to some embodiments, the rotation, vibration and/or precession of the cannula may facilitate irrigation and/or aspiration, reduce aspirate viscosity, reduce adhesive and friction forces, force liquids into the cannula, and/or prevent clogging of the cannula. The effects might be performed directly by the grinding wire or spring and/or by the turbulence sheer forces created in the propelled irrigates and/or sinus materials. According to some embodiments, the cannula's rotation, vibration, precession and/or back-and forth movement may propel sinus material and/or irrigates to the sinus ostium.

According to some embodiments, the flexible hollow cannula's rotation/precession is configured to allow fluid flow out of the sinus via the ostium, while the cannula is located within the ostium, thereby irrigating the sinus.

According to some embodiments, the rotation, vibration and/or precession of the cannula may enlarge the ostium once inserted therethrough. That is, without being bound by any theory, rotation, vibration and/or precession of the cannula may induce a gentle pressure on the walls of the ostium, thereby causing fluids and mucus absorbed therein to be expelled, thereby enlarging the ostium. According to some embodiments, the rotation, vibration and/or precession of the cannula, and thus the degree of force applied to the ostium walls, may be controllable. According to some embodiments, the ostium may be enlarged while preserving the mucosa and or the bones of the sinus cavity. According to some embodiments, the enlargement of the ostium may be atraumatic. However, according to some alternative embodiments, the pressure may be increased to cause bone fractures. According to some embodiments, the enlargement of the ostium may be reversible or irreversible. Each possibility is a separate embodiment.

According to some embodiments, the enlargement of the ostium may improve irrigation flow as well as evacuation of irrigates out of the sinus, thereby shortening the duration of the procedure.

According to some embodiments, the gentle ostia mucosal pressure is configured to prohibit or reduce pressure accumulation within the sinus by enabling air and liquids movement in and out of the sinus, for example during sinus irrigation and aspiration.

According to some embodiments, the rotation, vibration, precession and/or back-and forth movement of the grinding wire is configured only to remove sinus mucus while substantially preserving the sinus mucosa. According to some embodiments, the rotation, vibration, precession and/or back-and forth movement of the grinding wire is configured to remove sinus mucus and sinus pathogens, such as bacterial biofilm and fungi, while preserving most of the sinus mucosa. According to some embodiments, the rotation, vibration, precession and/or back-and forth movement of the grinding wire is configured to remove only the sinus mucosa, while leaving the sinus bone unharmed. According to some embodiments, the rotation, vibration, precession and/or back-and forth movement of the grinding wire is configured to remove only thickened and/or pathologic sinus mucosa while preserving healthy sinus mucosa.

According to some embodiments, the medical device may further include an actuator. The actuator may be configured to extend and withdraw the flexible hollow cannula from and into the elongated tubular member. According to some embodiments, the actuator may be configured to axially rotate the cannula within the elongated tubular member.

According to some embodiments, the flexible hollow cannula may be steerable. According to some embodiments, the actuator may be configured to steer the hollow cannula and/or the grinding wire to a treatment area. According to some embodiments, the medical device may further include a registration/navigation system configured to indicate a position of the flexible hollow cannula and/or flexible grinding wire in relation to the subject's anatomy or treatment area. The steerability/navigation of the hollow cannula and/or the flexible grinding wire serves to ensure that the desired treatment area is properly reached while guaranteeing maximum safety.

According to some embodiments, the treatment area is a lower part (lower third/quarter) of the paranasal sinus. According to some embodiments, the treatment area is the floor of the sinus cavity. According to some embodiments, the treatment area is the sinus medial side. According to some embodiments, the treatment area is the sinus dorsal side. According to some embodiments, the treatment area is defined by thickened or pathologic mucosa. According to some embodiments, the treatment area is defined by presence of fungi bacteria or photogenes. According to some embodiments, the treatment area is defined by its proximity to a potential anatomical risk such as a nerve, blood vessel, eye or weak bone. According to some embodiments, the treatment area is chosen by a device user to avoid anatomic potential hazard.

According to some embodiments, there is provided a medical device for treating a paranasal sinus condition, the medical device including an elongated tubular member having a distal end, the distal end is bent or bendable to face a natural opening of the paranasal sinus, and a hollow shaft, at least partially located within the elongated tubular member, the hollow shaft includes, at a distal end thereof, a protruding portion, wherein the protruding portion of the hollow shaft is configured to retractably extend from the distal end of the elongated tubular member, to penetrate through the natural opening of the paranasal sinus and to assume a predetermined relaxed bent shape at a treatment area within the paranasal sinus.

According to some embodiments, the hollow shaft includes a super-elastic material. According to some embodiments, the bent relaxed shape is an arc shape or L shape. According to some embodiments, the treatment area is a lower part (lower third/quarter) of the paranasal sinus. According to some embodiments, the super-elastic material is a pseudo-elastic material. According to some embodiments, the super-elastic material is a Nickel-Titanium alloy. According to some embodiments, the hollow shaft is configured to receive samples from the paranasal sinus.

According to some embodiments, the hollow shaft is configured to facilitate flow of a fluid material to the paranasal sinus. According to some embodiments, the fluid material is an irrigation material. According to some embodiments, the fluid material includes a pharmaceutically active ingredient. According to some embodiments, the fluid material includes bacteria.

According to some embodiments, the hollow shaft is configured for conducting aspiration from the paranasal sinus.

According to some embodiments, the device further includes an actuator configured to extend and withdraw the hollow shaft from and to the tubular member. According to some embodiments, the device further includes a control mechanism functionally associated with the hollow shaft for controlling the operation of the hollow shaft. According to some embodiments, the control mechanism is further configured to control irrigation, aspiration, sampling, administration of a pharmaceutically active material, bacteria or any combination thereof. According to some embodiments, the control mechanism is at least partially operated using a handle located at a proximal end of the tubular member.

According to some embodiments, the device further includes a pumping-orifice configured to provide fluid to the hollow shaft. According to some embodiments, the device further includes a suction-orifice configured to provide suction to the hollow shaft. According to some embodiments, the device further includes an illuminator configured to be threaded through the hollow shaft and to reach the paranasal sinus. According to some embodiments, the device further includes an illumination-orifice configured to provide illumination to the hollow shaft. According to some embodiments, the device further includes a container configured to receive samples obtained from the paranasal sinus and/or to provide a medicament bacteria and/or irrigation fluid to the paranasal sinus.

According to some embodiments, the device further includes a grinding element insertable through the hollow shaft for grinding mucus or tissue. According to some embodiments, the hollow shaft is rotatable for grinding mucus or tissue. According to some embodiments, the device further includes a nostril plug for sealing one or two nostrils.

According to some embodiments, there is provided a medical device for treating a paranasal sinus condition, the medical device including, a hollow shaft and a guide wire distal to the hollow shaft, the guide wire is configured to penetrate through a natural opening of the paranasal sinus and to facilitate the penetration of the hollow shaft through a natural opening.

According to some embodiments, the hollow shaft is connected to the guide wire by an outer tubular coating. According to some embodiments, the outer tubular coating is perforated to allow fluid flow through the hollow shaft.

According to some embodiments, the hollow shaft is connected to the guide wire by a collapsible connecting wire configured to collapse upon reaching the paranasal sinus, thereby to allow the hollow shaft to reach a treatment area at a lower part (lower third/quarter) of the paranasal sinus and to further allow fluid flow through the hollow shaft.

According to some embodiments, the guide wire is more flexible than the hollow shaft. According to some embodiments, the hollow shaft includes a super-elastic material.

According to some embodiments, the device further includes an elongated tubular member having a distal end, the distal end is bent or bendable to face a natural opening of the paranasal sinus, wherein the hollow shaft is at least partially retractably located within the elongated tubular member.

According to some embodiments, the device further includes a grinding element insertable through the hollow shaft for grinding mucus or tissue. According to some embodiments, the hollow shaft is rotatable for grinding mucus or tissue.

According to some embodiments, there is provided a medical device for treating a paranasal sinus condition, the medical device including, an elongated tubular member having a distal end, the distal end is bent or bendable to face a natural opening of the paranasal sinus, and a hollow shaft, at least partially located within the elongated tubular member, the hollow shaft includes, at a distal end thereof, a protruding portion, wherein the protruding portion of the hollow shaft is configured to retractably extend from the distal end of the elongated tubular member, to penetrate through the natural opening of the paranasal sinus, wherein the hollow shaft is rotatable for grinding mucus or tissue.

According to some embodiments, there is provided a method for treating a paranasal sinus condition, the method including approximating an elongated tubular member having a bent or bendable portion at a distal end thereof to a natural opening of a paranasal sinus, extending a hollow shaft material having a relaxed bent shape from the elongated tubular member through the natural opening such that the relaxed bent shape of the shaft reaches a treatment area at the paranasal sinus, and performing irrigation to and/or aspiration from the paranasal sinus.

According to some embodiments, the method further includes inserting a grinding element through the hollow shaft and grinding mucus or undesired tissue. According to some embodiments, the method further includes inserting an illuminator through the hollow shaft to the paranasal sinus and illuminating the paranasal sinus. According to some embodiments, the method further includes collecting a sample from the paranasal sinus. According to some embodiments, the method further includes administering medication and/or bacteria to the paranasal sinus.

According to some embodiments, there is provided a method for treating a paranasal sinus condition, the method including inserting a hollow shaft through a natural opening of a paranasal sinus such that a distal end of the shaft reaches a treatment area at the paranasal sinus, and inserting irrigation fluid to the paranasal sinus and/or collecting aspiration from the paranasal sinus, only through the natural opening of the paranasal sinus.

According to some embodiments, the method further includes inserting a grinding element through the hollow shaft and grinding mucus or undesired tissue. According to some embodiments, the method further includes inserting an illuminator through the hollow shaft to the paranasal sinus and illuminating the paranasal sinus. According to some embodiments, the method further includes collecting a sample from the paranasal sinus. According to some embodiments, the method further includes administering medication and/or bacteria to the paranasal sinus.

According to some embodiments, there is provided a method for treating a paranasal sinus condition, the method including inserting a hollow shaft through a natural opening of a paranasal sinus such that a distal end of the shaft reaches a treatment area at the paranasal sinus, and inserting a cutting element through the hollow shaft and cutting mucus or an undesired tissue.

According to some embodiments, there is provided a kit for treating a paranasal sinus condition, the kit including a hollow shaft including at a distal end thereof, a protruding portion shaped to penetrate a treatment area in the paranasal sinus through a natural opening thereof, and at least one of the following:

A container including irrigation fluid, medicament, bacteria or any combination thereof for administering to the paranasal sinus.

A container for sampling material obtained from the paranasal sinus.

According to some embodiments, the kit further includes a grinding element for inserting through the hollow shaft for grinding mucus or undesired tissue.

According to some embodiments, there is provided a kit for treating a paranasal sinus condition, the kit including a hollow shaft and a guide wire distal to the hollow shaft, the guide wire is configured to penetrate through a natural opening of the paranasal sinus and to facilitate the penetration of the hollow shaft through a natural opening, and at least one of the following:
- A container including irrigation fluid, medicament, bacteria or any combination thereof for administering to the paranasal sinus.
- A container for sampling material obtained from the paranasal sinus.

According to some embodiments, there is provided a kit for treating a paranasal sinus condition, the kit including a hollow shaft configured to penetrate through the natural opening of the paranasal sinus, wherein the hollow shaft is rotatable for grinding mucus or tissue, and at least one of the following:
- a container including irrigation fluid, medicament, bacteria or any combination thereof for administering to the paranasal sinus.
- a container for sampling material obtained from the paranasal sinus.

According to some embodiments, there is provided a medical device for treating a paranasal sinus condition and/or for sinus irrigation and/or aspiration, the medical device including a hollow shaft configured to be partially inserted into a sinus cavity and to suck material from the sinus, and a grinder configured to rotate within the hollow shaft at over 100 RPM, wherein the grinder is configured to grind, chop and/or stir the sucked material within the hollow shaft, thereby facilitating sucking through the hollow shaft.

According to some embodiments, the sucked material includes mucus. According to some embodiments, the sucked material includes soft tissue. According to some embodiments, the soft tissue includes mucosa and/or polyps. According to some embodiments, the device is further configured to irrigate the sucked material. According to some embodiments, the device further includes an engine configured to rotate the grinder.

According to some embodiments, there is provided a medical device for treating a paranasal sinus condition and/or for sinus irrigation and/or aspiration, the medical device including a hollow shaft configured to be partially inserted into a sinus cavity and to suck material from the sinus, and a grinder configured to be inserted into the sinus cavity through the hollow shaft, to protrude out of a distal end of the hollow shaft into the sinus cavity, to assume predetermined shape inside the sinus cavity and to rotate within the sinus cavity at over 100 RPM, wherein the grinder is configured to grind, chop and or stir material within the sinus cavity, thereby facilitating sucking the material through the hollow shaft, or evacuating the material through a sinus ostium.

According to some embodiments, the material includes mucus. According to some embodiments, the material includes soft tissue. According to some embodiments, the soft tissue comprises mucosa and/or polyps. According to some embodiments, the material includes bacteria, fungi or both. According to some embodiments, the device is further configured to irrigate the material and/or the sinus cavity.

According to some embodiments, the grinder is configured not to harm the sinus bone, the sinus mucosa or both. According to some embodiments, the grinder is configured not to harm only a part of the sinus mucosa. According to some embodiments, the part of the sinus mucosa is the mucosa that does not cover a treatment area. According to some embodiments, the part of the sinus mucosa is the underside of the sinus mucosa.

According to some embodiments, a distal end of the hallow shaft is configured to change its position inside the sinus and to direct the grinder to a treatment area. According to some embodiments, a distal end of the hallow shaft is configured to change position to a predetermined shape inside the sinus and direct the grinder to a treatment area.

According to some embodiments, the grinder is further configured to stir irrigation liquids and cause turbulence in the irrigation. According to some embodiments, the grinder is configured to stir the material with irrigation fluids that contain one or more therapeutic sub stance.

According to some embodiments, assuming predetermined shape inside the sinus results from the grinder elasticity or pseudo-elasticity. According to some embodiments, assuming predetermined shape inside the sinus results from centrifugal force and/or sinus material resistance.

According to some embodiments, the grinder is configured to propel grinded material and/or irrigation liquids towards a sinus ostium. According to some embodiments, the grinder is configured to be inserted through natural sinus ostium without surgical dilation or expansion. According to some embodiments, the grinder is configured to be inserted through sinus ostium after ostial balloon dilation.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions. It is understood that certain elements or configurations illustrated in a specific figure/embodiment may be included in other figures/embodiment and that various combination of elements and/or configurations are possible.

Reference is now made to FIG. 1, which schematically illustrates a device 100 for treating a paranasal sinus condition, according to some embodiments. Device 100 has a tubular member 102 with a distal end 104. Distal end 104 is configured for insertion into a nostril of a patient and is at least partially bent and/or bendable to face a natural opening of a paranasal sinus. Device 100 also has a hollow shaft 106 movably located within tubular member 102 and a protruding portion 108 of hollow shaft 106 is configured to extend from distal end 104 and assume a predefined relaxed shape configured to reach a treatment area within a paranasal sinus.

Device 100 further includes a handle 110 mechanically connected to tubular member 102 at a proximal end thereof. Handle 110 hosts an actuator 112 configured to control movement and extension of hollow shaft 106 within and beyond tubular member 102. A pumping-orifice 114, a tool-orifice 115 and a suction-orifice 116 are positioned on handle 110. Pumping-orifice 114 configured to provide fluid to hollow shaft 106 and suction-orifice 116 is configured to provide suction to hollow shaft 106. Handle 110 further hosts a detachable container 118 configured to contain medicament to be delivered to a paranasal sinus treatment area and/or to collect samples extracted therefrom. A nostril-plug 120 is mounted on tubular member 102 and shaped to at least partially block the nostrils of a subject. According to some embodiments, nostril-plug 120 has a first aperture 122 and a second aperture 124 configured to be mechanically connected to a first tube 126 and a second tube 128 respectively. According to some embodiments, first aperture 122, first tube 126 and tubular member 102 are co-centric. First aperture 122 and first tube 126 may be utilized for delivering fluids to a nasal cavity of the patient, while second aperture 124 and second tube 128 may be utilized for sucking fluids from the nasal cavity of the patient. According to other embodiments, fluids can be delivered through second aperture 124 and second tube 128 and removed through first aperture 122 and first tube 126.

According to some embodiments, pumping-orifice 114, tool-orifice 115 and suction-orifice 116 are sealed.

According to some embodiments, tool-orifice 115 may facilitate passage of an illumination element to provide illumination in the treatment area and/or to assist in determining the location of distal-end 104 and/or protruding portion 108. According to some embodiments, tool-orifice 115 may facilitate passage of tools through hollow shaft 108 and/or tubular member 104 to a paranasal sinus or a treatment area therein. Such tools may comprise needles, grinders, measurement instruments, blades, guide-wires, directional fluid jet and others.

According to some embodiments, actuator 112 is configured to be manually controlled by a healthcare provider.

According to some embodiments, nostril-plug 120 may enable treatment of a patient while the patient is in a resting/relaxed position. According to some embodiments, the relaxed position may be a laid-back position. Advantageously, having a patient lay in a relaxed position may result in better adherence and less anxiety during and towards the treatment.

Figure 2:
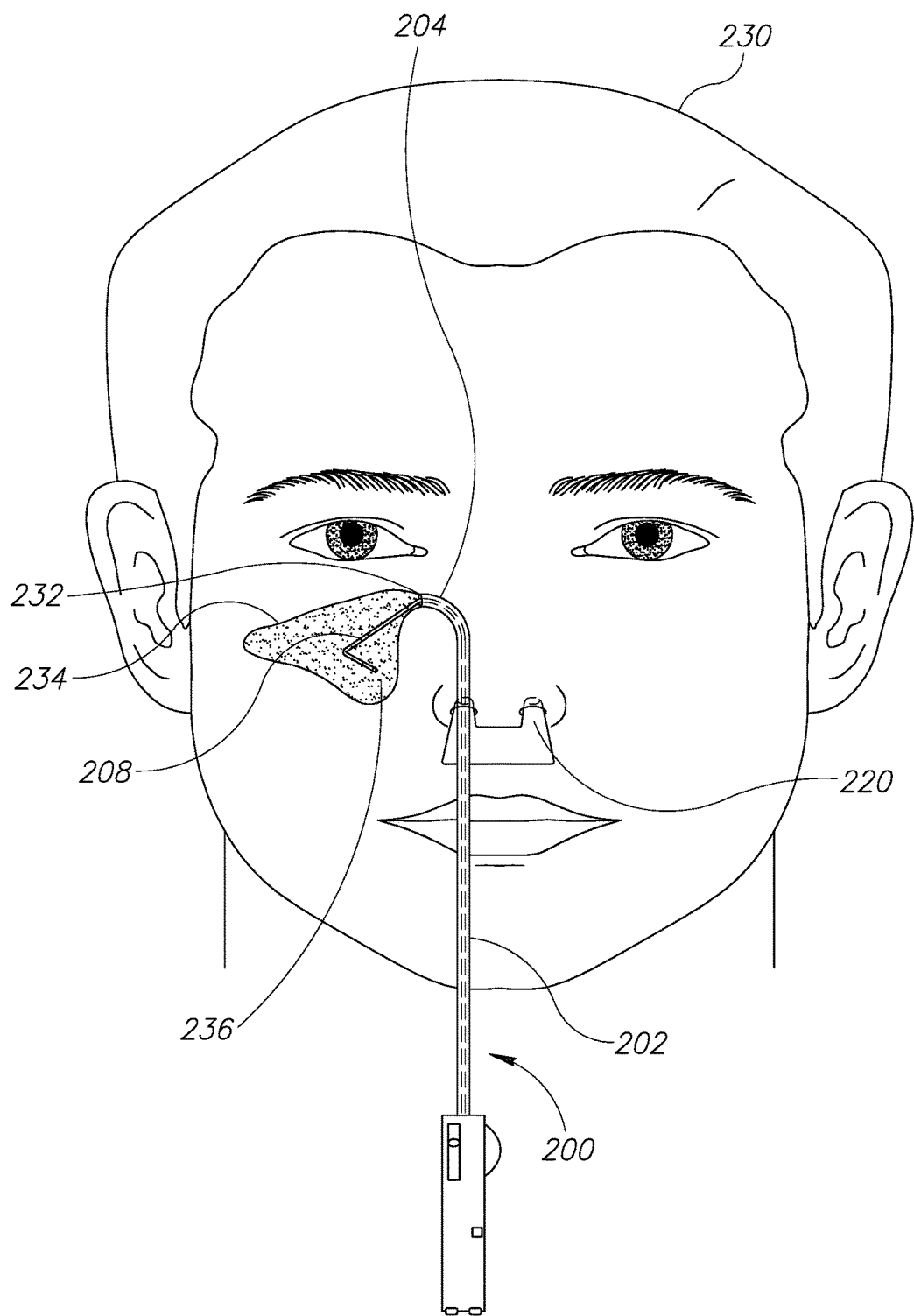
FIG. 2 schematically illustrates a device for treating a paranasal sinus condition during treatment, according to some embodiments.

Reference is now made to FIG. 2, which schematically illustrates a device 200 for treating a paranasal sinus condition during treatment, according to some embodiments. Device 200 has a tubular member 202 with a distal end 204. Distal end 204 is inserted into a nostril of a patient 230 and is at least partially bent and/or bendable to face a natural opening 232 of a paranasal sinus 234. A protruding portion of a hollow shaft 208 is extended from distal end 204 and obtains a relaxed shape within paranasal sinus 234 reaching a treatment area 236. A nostril-plug 220 is mounted on tubular member 202 and blocks the nostrils of patient 230.

According to some embodiments, a treatment area within a paranasal sinus may be a lower half of a paranasal sinus cavity. According to some embodiments, the treatment area within a paranasal sinus may be a lower third of a paranasal sinus cavity. According to some embodiments, a treatment area within a paranasal sinus may be a lower quarter of a paranasal sinus cavity. According to some embodiments, a treatment area within a paranasal sinus may be in an area with mucosal over growth or mucosal disease, such as polyps, polypoid tissue, mucosal overgrowth, fungi, tumor or nonmalignant tumor.

According to some embodiments, the device is configured to treat and/or diagnose conditions on one or more of the following: a frontal sinus, a sphenoidal sinus, a maxillary sinus, an ethmoidal sinus, a Eustachian tube and/or other relevant treatment areas. According to some embodiments, the bent/bendable tip of the tubular member and/or the protruding portion of the hollow shaft are designed to reach a treatment area in at least one of the aforementioned areas. According to some embodiments, each area requires a different shape for reaching a treatment area therein.

According to some embodiments, the shape of the bendable/bent tip of the tubular member and the shape of the protruding portion of the hollow shaft form a non-planar shape in space.

According to some embodiments, the distal end of the tubular member is bendable, and the bending may be done during or prior to inserting the distal end of the shaft into a nostril of a patient. Advantageously, the bending of the distal end guides the protrusion of the hollow shaft through the natural opening of the paranasal sinus.

According to some embodiments, the distal end of the tubular member is made at least partially from bendable material. According to some embodiments, the plasticity of the distal end of the tubular member is lower than the plasticity of the hollow shaft such that the shaft may be strained by the bent shape of the distal end of the tubular member when it passes through. According to some embodiments, the distal end is "U" shaped. According to some embodiments the distal end is "J" shaped. According to some embodiments the distal end is "V" shaped.

According to some embodiments, the protruding portion of the hollow shaft has a predetermined relaxed shape obtained upon extending from the distal end. According to some embodiments, the hollow shaft has an opening configured to facilitate passage of medication, mucus, soft tissue, fluid, illumination devices, diagnostic equipment, treatment equipment such as grinders, balloons or blades, and/or any combination thereof. Each possibility is separate embodiment, According to some embodiments, the predetermined relaxed shape of the protruding portion may comprise relatively straight lines, bent lines, acute angles, obtuse angles, right angles, sharp bends, slight bends and/or any combination thereof. Each possibility is separate embodiment, Reference is now made to FIG. 3a-FIG. 3f, which schematically illustrate a protruding portion of a hollow shaft in various relaxed shapes, according to some embodiments. A protruding portion 304 of hollow shaft 303 of device 300 is extended from a distal end 302 of a tubular member through a natural opening 332 of a paranasal sinus. Protruding portion 304 of hollow shaft 303 has an opening 306 configured to enable treatment and/or diagnosis for a treatment area of a paranasal sinus.

Figure 3A:
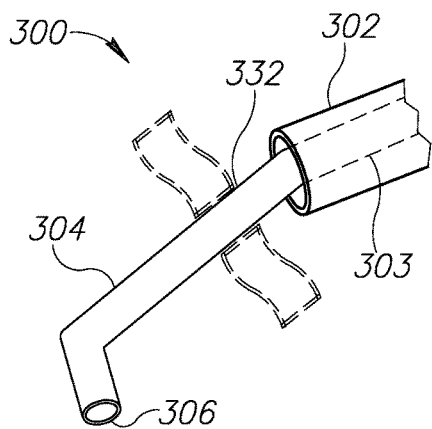
FIG. 3a-FIG. 3f schematically illustrate a protruding portion of a hollow shaft in various relaxed shapes, according to some embodiments.

In FIG. 3a protruding portion 304 has a relaxed shape comprising straight lines with an acute angle and opening 306 facing downwards.

Figure 3B:
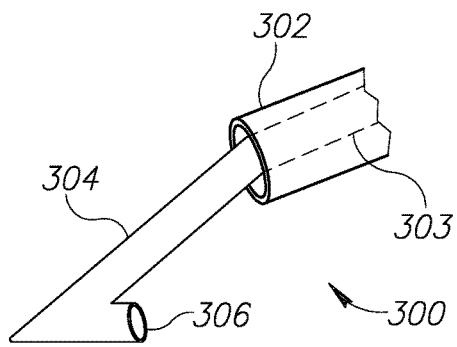

In FIG. 3b protruding portion 304 has a relaxed shape comprising straight lines with an obtuse angle and opening 306 facing upwards.

Figure 3C:
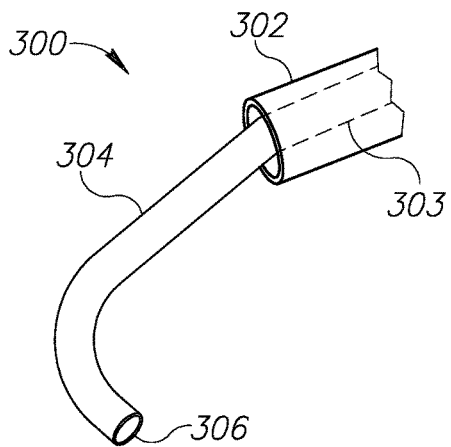

In FIG. 3c protruding portion 304 has a relaxed shape comprising straight lines with a wide bend and opening 306 facing downwards.

Figure 3D:
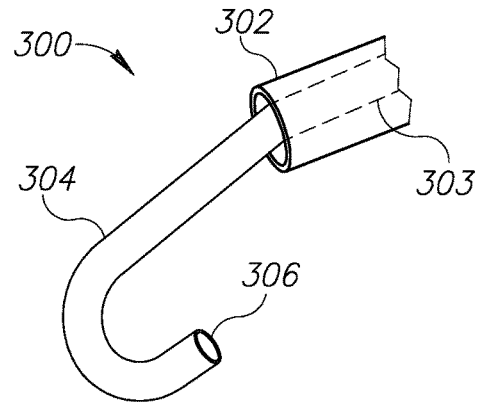

In FIG. 3d protruding portion 304 has a relaxed shape comprising straight lines with a sharp bend and opening 306 facing upwards.

Figure 3E:
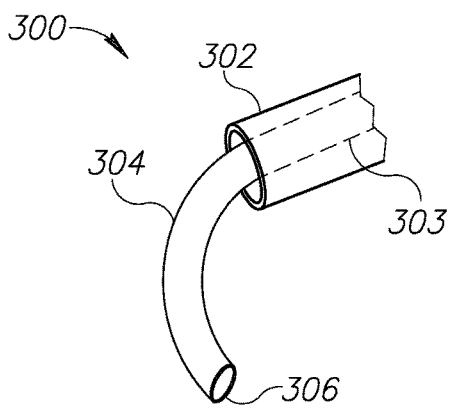

In FIG. 3e protruding portion 304 has a relaxed shape comprising curved lines with a wide bend and opening 306 facing downwards.

Figure 3F:
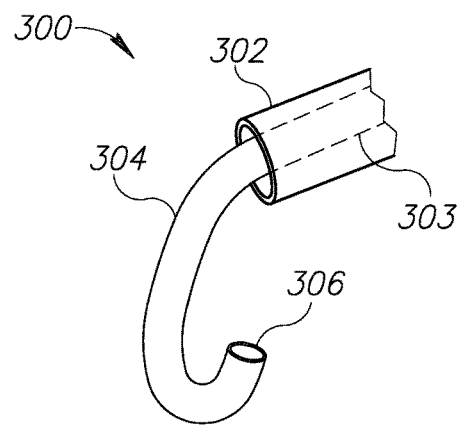

In FIG. 3f protruding portion 304 has a relaxed shape comprising curved lines with a sharp bend and opening 306 facing upwards. Having protruding portion 304 of hollow shaft 303 with opening 306 facing downwards may be advantageous for reaching a lower end of a paranasal sinus. Having protruding portion 304 of hollow shaft 303 with opening 306 facing downwards may be advantageous for applying various tools such as a grinder, suction, or a fluid jet within the paranasal sinus.

According to some embodiments, the opening of the protruding portion is circular having an inner radius of approximately 1.2 mm and an outer radius of approximately 1.5 mm. According to some embodiments, the opening of the protruding portion is circular having an inner radius of approximately 1 mm and an outer radius of approximately 1.2 mm. According to some embodiments, the opening of the protruding portion is circular having an inner radius of approximately 0.8 mm and an outer radius of approximately 1 mm. According to some embodiments, the opening of the protruding portion is circular having an inner radius of approximately 0.6 mm and an outer radius of approximately 0.8 mm.

According to some embodiments, the opening of the protruding portion is elliptical, circular, regular or non-regular shape having a cross-section surface area in the range of 0.5 mm$^2$ to 1.5 mm$^2$ such as, but not limited to, a cross-section surface area of approximately 0.785 mm$^2$.

According to some embodiments, the hollow shaft has a wall thickness in the range of 0.05 mm to 0.5 mm, such as, but not limited to, a wall thickness of approximately 0.1 mm.

According to some embodiments, the opening of the distal end of the tubular member is circular having a radius in the range of 0.5 mm to 1.5 mm$^2$ such as, but not limited to, a radius of approximately 1 mm.

According to some embodiments, the opening of the distal end of the tubular member is elliptical, circular, regular or non-regular shape having a cross-section surface area in the range of 2 mm$^2$ to 4.5 mm$^2$ such as, but not limited to, a cross-section surface area of approximately 3.14 mm$^2$.

According to some embodiments, the tubular member is made from plastic, metal, metal-alloy, silicon and/or other elastic materials. Each possibility is a separate embodiment.

According to some embodiments, the tubular member is at least partially coated with a non-toxic material.

According to some embodiments, the hollow shaft is at least partially coated with a non-toxic material such as hydrophilic coating, soft coating, smooth coating or lubricated coating. Each possibility is a separate embodiment.

Figure 4A:
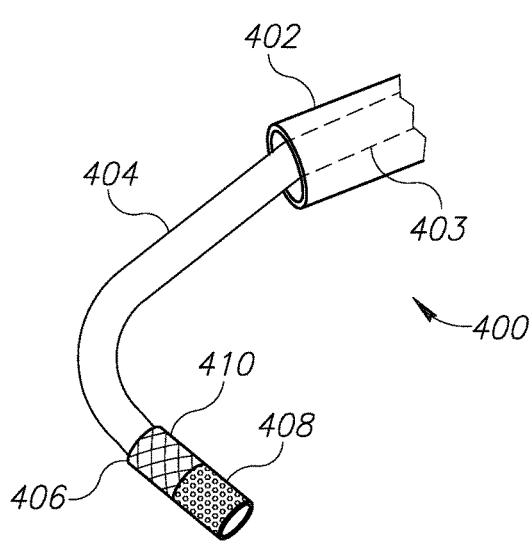
FIG. 4a-FIG. 4b schematically illustrate a protruding portion of a hollow shaft with a penetration facilitation element, according to some embodiments.
Figure 4B:
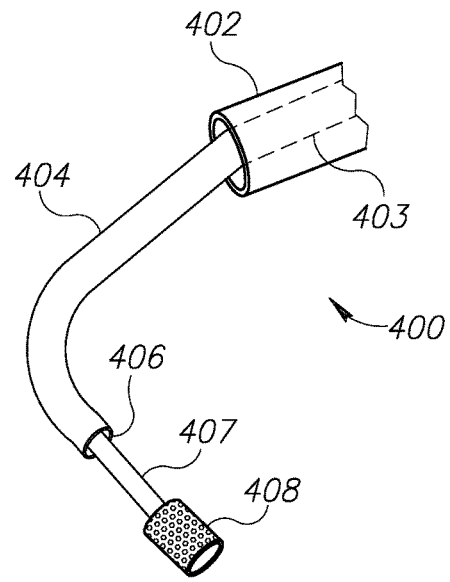

Reference is now made to FIG. 4a-FIG. 4b, which schematically illustrate a device 400 having a protruding portion 404 of a hollow shaft 403 extended from distal end 402 of a tubular member with a penetration facilitation element such as a guide-wire 408. According to some embodiments the penetration facilitation element is located distally to the distal opening 406 of hollow shaft 403 and is configured to facilitate the penetration of the hollow shaft through the natural opening of the sinus while protecting the inner walls of the sinus and preventing its damaging by the hollow shaft's walls. The penetration facilitation element is shown as guide-wire 408 but it is noted that it may also have a ball shape (e.g., silicon, polymeric or metal ball), a tube shape or any other appropriate shape as seen, for example, in FIGS. 6a-e.

In FIG. 4a, according to some embodiments, a net structure 410 connects penetration facilitation element 408 with an opening 406 of protruding portion 404. According to some embodiments, guide-wire 408 is elastic and configured to assist in guiding protruding portion 404 though the natural opening of the paranasal sinus without impacting or harming surrounding tissues. According to some embodiments, net structure 410 is configures to allow delivery of medicament and/or other fluids from opening 406 to the treatment area within the paranasal sinus. According to some embodiments, net structure 410 is configures to allow withdrawal of mucus and/or other fluids from the treatment area within the paranasal sinus to opening 406. According to some embodiments, net structure 410 is configure to allow insertion of a therapeutic device into the sinus, such as a grinder.

In FIG. 4b, according to some embodiments, an elastic band 407 connects penetration facilitation element 408 with the hollow shaft 404.

According to some embodiments, net structure 410 and elastic band 407 are made from an elastic material such as plastic, silicone or elastic alloy such as stainless steel or nitinol. According to some embodiments, net structure 410 or elastic band 407, bends with contact with the sinus wall or sinus bottom.

According to some embodiments, the guide-wire and/or the net structure obstruct direct flow of large objects to the opening of the protruding portion, advantageously preventing clogging of the opening. According to some embodiments, the guide-wire and/or the net structure create turbulence in the fluids being sucked and/or delivered to/from the paranasal sinus, advantageously availing an improved flow of fluids.

Figure 5A:
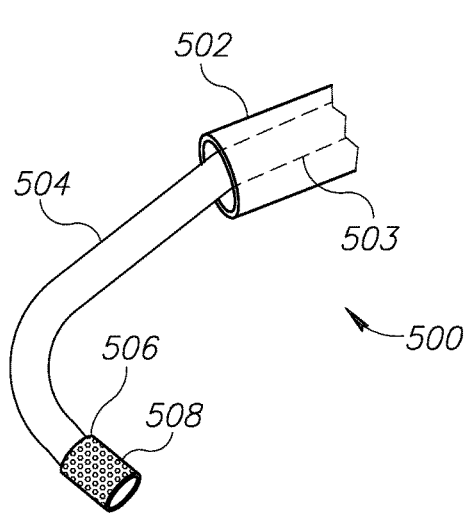
FIG. 5a-FIG. 5b schematically illustrate a protruding portion of a hollow shaft with a guide-wire in two positions, according to some embodiments.
Figure 5B:
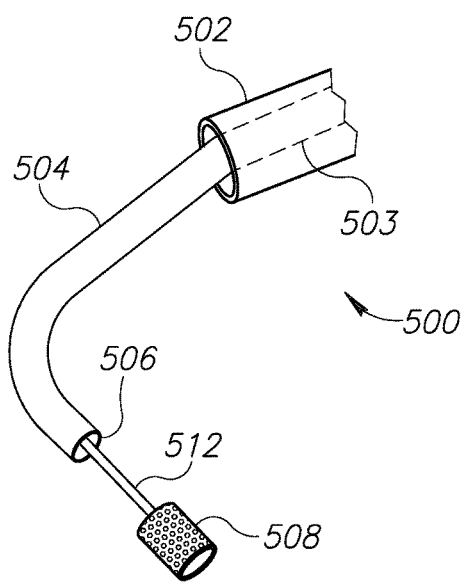

Reference is now made to FIG. 5a-FIG. 5b, which schematically illustrate a device 500 having a protruding portion 504 of a hollow shaft 503 having an opening 506 extended from a distal end 502 of a tubular member and a guide-wire 508 in two positions, according to some embodiments. According to some embodiments, guide-wire 508 is mechanically connected to a rod 512 configured to controllably fasten guide-wire 508 to opening 506 and to release it, thereby unblocking opening 506.

FIG. 5a schematically illustrates a position in which guide-wire 508 is fastened to opening 506, providing structural support to guide protruding portion 504 harmlessly through the natural opening of the sinus.

FIG. 5b schematically illustrates a position in which guide-wire 508 is furthered from opening 506, allowing insertion of therapeutic devices and flow of fluids to/from opening 506.

One challenge facing a healthcare provider during the procedure is inserting the protruding portion through the natural opening of the paranasal sinus without harming surrounding tissue. According to some embodiments, a guide wire is introduced to the protruding portion of the hollow shaft to assist/guide the protruding portion through the natural opening of the paranasal sinus. According to some embodiments, the guide-wire is made from elastic material configured to facilitate safe/harmless insertion of the protruding portion through the natural opening.

According to some embodiments, the guide-wire is mechanically connected to the protruding portion using a rod, a band or a net. According to some embodiments, the mechanical connection holds the guide-wire in an approximately fixed distance from the opening without opening and closing the opening of the protruding portion.

Reference is now made to FIG. 6a-FIG. 6e, which illustrate a protruding portion 604 of a hollow shaft with a penetration facilitation element 608 having different shapes and structures, according to some embodiments.

In FIG. 6a, penetration facilitation element 608 is designed to have a cylindrical shape.

In FIG. 6b, penetration facilitation element 608 is designed to have a cone shape.

In FIG. 6c, penetration facilitation element 608 is designed to have a spherical shape.

In FIG. 6d, penetration facilitation element 608 is designed to have a meniscus shape.

In FIG. 6e, penetration facilitation element 608 is designed to have a hollow-cylindrical shape. According to some embodiments, the penetration facilitation element provides protection to the sinus from the hollow shaft and movements thereof. According to some embodiments, the penetration facilitation element is a conventional guide-wire.

The mucus within the paranasal sinus may be difficult to suck out through the hollow shaft, especially given its small opening area (the natural opening of the paranasal generally gets smaller/tighter under the effects of various paranasal sinus conditions. Those conditions also may cause the mucus to be thicker). In some cases the walls of the paranasal sinuses are covered with bacteria. According to some embodiments, a grinder is introduced at the protruding portion to grind/chop/stir the mucus, thereby making it more fluid and easier to suck through the hollow shaft.

According to some embodiments, the grinder stirs irrigation liquids, such as water, with or without additive, within the sinus, causing the liquids turbulence to further grind materials in the sinus cavity such as mucus, bacteria that covers the sinus walls within the sinus, polyps, soft tissues and other relevant materials.

According to some embodiments, the device further comprises a grinder configured to extend from the protruding portion of the hollow shaft and grind mucus or other relevant material, such as biofilm, polyps or mucosal soft tissues. Advantageously, the grinding of mucus allows for easier suction using low suction pressure and/or smaller dimensions of the hollow shaft. Advantageously, the grinding of mucus allows avoiding surgical dilation of the sinus opening or sinus puncturing. Advantageously, the grinding of mucus and other materials allows a faster treatment. It is noted that, according to some embodiments, the device includes the hollow shaft (with or without the grinding element) but without the need of a tubular member. Such device may be directly inserted into the sinus through the natural opening of the sinus and may be operated and used as described herein.

It is also noted that, according to some embodiments, the device as described herein may be used following a procedure of expanding the natural opening of the sinus using a balloon or any other method.

It is also noted that, according to some embodiments, the device as described herein may be used for treating the sinus by puncturing the external wall of the sinus.

According to some embodiments, the grinder is configured to rotate axially, thereby impacting the target material and breaking the structure thereof. According to some embodiments, the grinder is made from plastic, such as nylon, metal such as steel alloy such as nitinol or the like. According to some embodiments, the grinder, or parts thereof, is made from bio-absorbable materials.

According to some embodiments, the axial rotation of the grinder extends portions of the grinder outwards, generating a larger rotation diameter, thereby obtaining a more significant momentum from the same rotation speed of the grinder. According to some embodiments, the grinder comprises a rope, a thread, an elastic sphere, a brush-shaped thread structure, a guide-wire, a brush with various thread lengths, a bent/bendable rod, or multiple rods connected to an axially rotating shaft. Each possibility is a separate embodiment.

According to some embodiments, the grinder is introduced into the sinus cavity within a hollow tubular member or a hollow shaft. The grinder distal part is small enough (e.g., having a diameter of about 0.1-0.5 mm) in comparison to the hollow tubular member or a hollow shaft distal end, to allow irrigation and aspiration during grinding. According to some embodiments, the grinder rotation can flow and direct the irrigation liquids within the sinus. The direction can be towards a certain sinus region, such as the sinus bottom, the sinus wall or the sinus opening. According to some embodiments, the flow direction can be determined according to the grinder shape, the grinder and hollow shaft position within the sinus, and/or the rotation direction. Each possibility is a separate embodiment.

According to some embodiments, the grinder provides grinding of a target object up to a granularity of approximately 0.1 mm. According to some embodiments, the grinder comprises a nitinol rope. According to some embodiments, the grinder comprises a cable, for example, a cable made by at least two wires or strands, which are twisted or braided together. According to some embodiments, the grinder comprises a lattice structure of elastic material. According to some embodiments, the grinder comprises a bio-absorbable material. According to some embodiments, the grinder may include more than one structures and/or materials. As a non-limiting example, the grinder may at one part thereof be made of a nitinol rope and at another section be made of a cable.

According to some embodiments, the grinder is at least partially coated with a non-toxic material. According to some embodiments, the grinder is coated with a hydrophobic softer material, such as silicon or rubber to reduce the impact on the mucosa, or with smooth material, such as Teflon.

According to some embodiments, the grinder is actuated by a motor in the handle. According to some embodiments, the grinder is hydraulically actuated. According to some embodiments, the grinder is actuated manually by a healthcare provider.

According to some embodiments, the grinder is designed to grind target material such as mucus, biofilm, polyps, without harming viable tissues in the paranasal sinus such as the bones or the mucosa.

According to some embodiments, the grinder has an axial rotation speed of approximately 10,000 RPM. According to some embodiments, the grinder has an axial rotation speed of between 100 RPM and 50,000 RPM. According to some embodiments, the grinder has an axial rotation speed of between 1,000 RPM and 20,000 RPM.

According to some embodiments, the grinding wire may rotate in one direction, e.g. clockwise or anti-clockwise rotation. According to some embodiments, the direction of rotation may change during use. For example, the grinder may perform a predetermined amount of rotation in a clockwise direction followed by a predetermined direction in an anti-clockwise direction or vice versa. According to some embodiments, the predetermined number of rotation may be same or different for each direction. According to some embodiments, the direction of rotation may change at predetermined time intervals, for example every 20 second, every 1 minute or any other suitable time interval.

Reference is now made to FIG. 7a-FIG. 7g, which schematically illustrate a device 700 having a protruding portion 704 of a hollow shaft 703 extended from a distal end 702 of a tubular member with a grinder 716 extending from opening 706, according to some embodiments. According to some embodiments, grinder 716 is an "L" shaped structure. According to some embodiments, grinder 716 is a "J" shaped structure. According to some embodiments, grinder 716 is a "V" shaped structure.

In FIG. 7a, grinder 716 is shown in a rotating position, extended outwards affected by centrifugal forces, and in a first position 715, prior to the rotation of the grinder. According to some embodiments, grinder 716 comprises an elastic rod or string. According to additional embodiments, the grinder distal end returns to its predetermined rotating position 716 due to elastic or memory shape forces.

In FIG. 7b, grinder 716 is an elastic rod having multiple elastic rods or threads connected to it.

In FIG. 7c, grinder 716 is a brush.

In FIG. 7d, grinder 716 is an elastic rod or thread having an elastic sphere connected to it.

In FIG. 7e, grinder 716 is an elastic brush having various threads. The threads can have various lengths, shapes and rigidity levels.

In FIG. 7f, grinder 716 is an elastic rod with a penetration facilitation element such a guide-wire connected to it. According to some embodiments, the guide-wire double functions as a guide-wire and as a grinder.

In FIG. 7g, grinder 716 is an elastic net or cable structure. According to some embodiments the grinder can be the rope on its own. According to additional embodiments, the sphere in the distal end of the grinder can be woven or tied from the cable strings.

According to some embodiments, a grinder may be at least partially made from carbon. According to some embodiments, the grinder may be at least partially made from carbon-nano-tubes.

According to some embodiments, a grinder may have MEMS (micro-electro-mechanical-structure) in various parts thereof to provide control to the shape of the grinder.

According to some embodiments, the shape of the grinder is controllable using electro-magnetic waves/signals.

According to some embodiments, the grinder has elastic threads with silicon on the tips of the threads. According to some embodiments, the threads are made from nitinol.

According to some embodiments, different shapes, materials, rotation speeds and/or elasticity of various grinders allow for selective controllable grinding of desired tissues/targets within the paranasal sinus. According to some embodiments, a target may be, for example: germs, mucus, fungus, polyp, lining, tumor and/or others.

According to some embodiments, the grinding process generates a mixture of air, water and/or mucosal liquids thereby easing the suction process thereof.

Advantageously, the grinding process enables sucking the grinded material through a 1 mm hollow shaft.

Advantageously, water pressure may provide dilation of the ostium around the hollow shaft and pressurize mucus around the ostium.

According to some embodiments, axial rotation of grinder 716 is actuated by a motor in the handle of the device.

According to some embodiments, the grinder may be made of multiple materials having different properties such as elasticity and rigidity. Such complex structure/composition may assist in grinding mucus/polyps while not causing significant harm to the bone and mucosa on the sinus walls. An example of such complex structure/composition may include long and short fibers (hair) (see for example FIG. 7e). The long fibers may be made of softer material, such as nylon and the short hair may be made of stiffer material, such as Nitinol.

Figure 8:
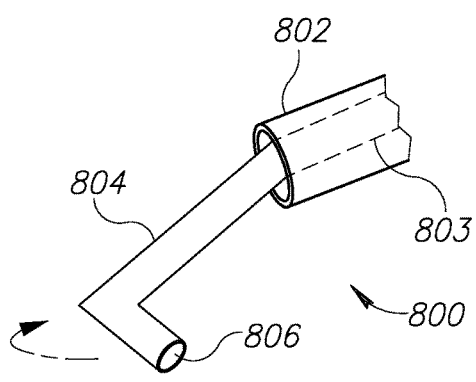
FIG. 8 schematically illustrates a rotating protruding portion of a hollow shaft, according to some embodiments.

Reference is now made to FIG. 8, which schematically illustrates device 800 having a protruding portion 804 of a hollow shaft 803 extended from a distal end 802 of a tubular member and opening 806 pointing downwards. Protruding portion 804 is configured to rotate axially and provide grinding capabilities, according to some embodiments. According to some embodiments, protruding portion 804 is configured to be rotatable within the paranasal sinus cavity. This is an exemplary optional configuration that may or may not replace a dedicated grinder.

According to some embodiments, the hollow shaft, the protruding portion of the hollow shaft and/or other portions thereof host a flow-assisting structure/mechanism and/or an internal grinder. According to some embodiments, the internal grinder is configured to assist in delivering material extracted from a treatment area through the hollow shaft. According to some embodiments, the internal grinder is configured to stir material extracted from a treatment area and to allow a continuous flow of the material through the hollow shaft. The internal grinder can work during irrigation and aspiration with the hollow shaft.

According to some embodiments, the internal grinder is configured to prevent residues of material from sticking to the insides of the hollow shaft. According to some embodiments, the internal grinder is configured to grind and/or chop material extracted from a treatment area to allow for enhanced flow of the material through the hollow shaft. According to some embodiments, the internal grinder is configured to continually apply pressure on mucus material, denying it from becoming thicker (the mucus is non Newtonian liquid or visco-elastic gel that responds to pressure by reducing its viscosity). According to some embodiments, the internal grinder is configured to continually blend the residues of material with liquids, thereby preventing it from drying.

According to some embodiments the internal grinder is configured to continually blend and/or stir liquids within a sinus cavity. The internal grinder may or may not protrude out or from the tube opening, in order to blend and/or stir the liquids.

According to some embodiments the internal grinder is configured to be used not only during irrigation and aspiration, but also to clean the hollow shaft. According to some embodiments, the internal grinder may clean the hollow shaft in conjunction with a cleaning agent such as water, soap or disinfectors. Each possibility is a separate embodiment.

According to some embodiments, the internal grinder may comprise an Archimedes screw structure, a rotating wire/thread, a movable rod, a movable brush, a movable tube, a spiral and/or a spring and the like. Each possibility is a separate embodiment of the disclosure.

According to some embodiments, the internal grinder may rotate axially and/or move along the hollow shaft.

Reference is now made to FIG. 9a-FIG. 9f, which schematically illustrate device 900 having a protruding portion 904 of a hollow shaft 903 extended from a distal end 902 of a tubular member and opening 906 pointing downwards. Protruding portion 904 of a hollow shaft 903 hosts an internal grinder 918.

Figure 9A:
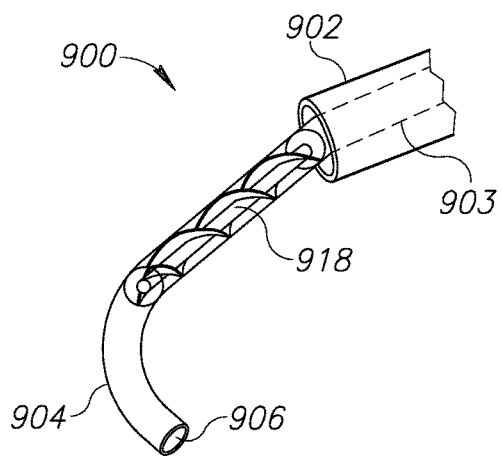
FIG. 9a-FIG. 9f schematically illustrate a protruding portion of a hollow shaft with various flow-assist structures, according to some embodiments.

In FIG. 9a, internal grinder 918 is an Archimedes screw, according to some embodiments. The Archimedes screw assists in sucking material through the hollow shaft by rotating spiral blades axially pulling direction, thereby providing suction forced to assist with continuous flow of material and advantageously prevent clogging.

Figure 9B:
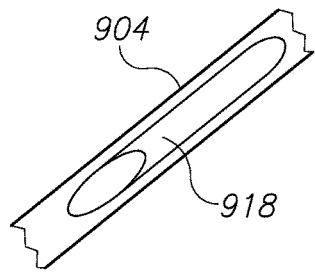

In FIG. 9b, internal grinder 918 is a hollow tube, according to some embodiments. According to some embodiments, the hollow tube is movable within hollow shaft 904. According to some embodiments, the hollow internal grinder 918 is used as a suction channel for withdrawing the grinded material out of the sinus cavity. It is understood that the rotation, vibration, precession and/or back and forth movement of the grinding wire reduces the friction of the material and thus its viscosity, thereby easing the suction out of the material.

Figure 9C:
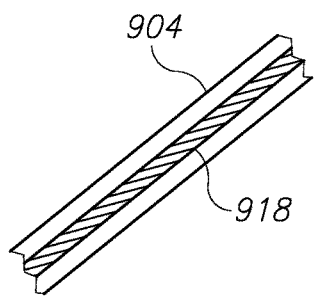

In FIG. 9c, internal grinder 918 is an elastic rod, according to some embodiments. According to some embodiments, the elastic is movable within hollow shaft 904.

Figure 9D:
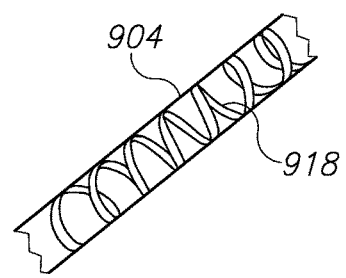

In FIG. 9d, internal grinder 918 is a rotating spring, according to some embodiments. According to some embodiments, the spring is movable within hollow shaft 904.

Figure 9E:
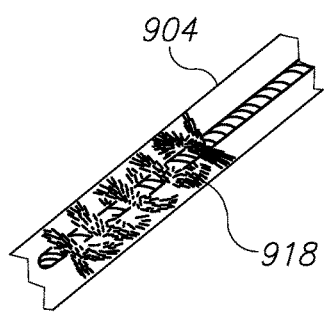

In FIG. 9e, internal grinder 918 is a rotating brush, according to some embodiments. According to some embodiments, the brush is movable within hollow shaft 904.

Figure 9F:
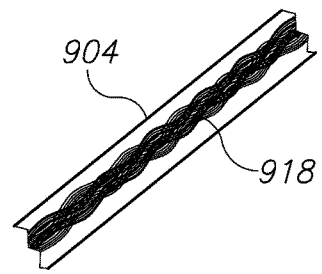

In FIG. 9f, internal grinder 918 is an elastic rope, according to some embodiments. According to some embodiments, the rope is movable within hollow shaft 904.

Reference is now made to FIGS. 10a-i, which schematically illustrate protruding portions 1004 of a hollow shaft with a grinder 1016 extending from opening 1006, according to some embodiments. According to some embodiments, grinder 1016 is a wire. According to some embodiments, grinder 1016 may include various structures and/or configurations as further illustrated hereinbelow. The structures exemplified below are illustrative only and additional configurations/structures are also applicable and thus within the scope of this disclosure. According to some embodiments, the structure/configuration may be pre-formed. Alternatively, the structure/configuration may be generated/activated once grinder 1016 reaches the designated treatment area. Grinder 1016 is here illustrated as being external to protruding section 1004; however other configurations in which grinder 1016 is located entirely, mostly or partially within protruding section 1004 are also envisaged and as such within the scope of the present disclosure.

Figure 10A:
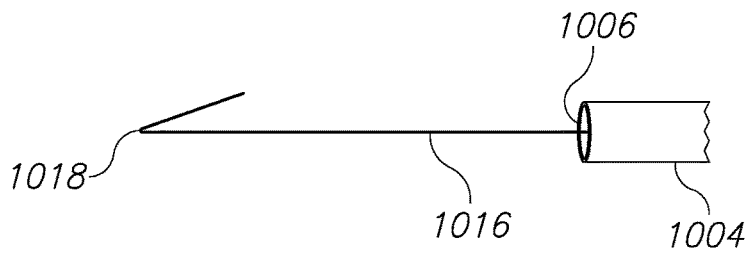
FIG. 10a-FIG. 10i schematically illustrate a protruding portion of a hollow shaft with a grinder extending from a distal opening thereof, according to some embodiments.

In FIG. 10a, grinder 1016 comprises an elastic rod, string or wire. According to additional embodiments, grinder 1016 includes a kink 1018 generating a hook structure.

Figure 10B:
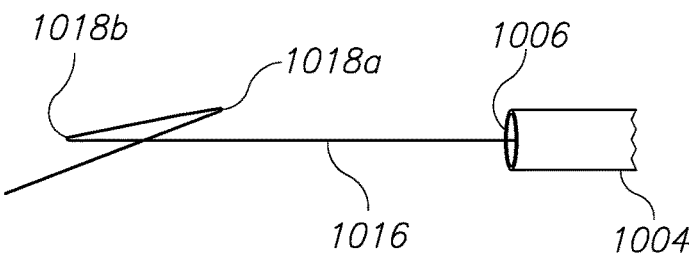

In FIG. 10b, grinder 1016 is an elastic rod, string or wire including two kinks, kinks 1018a and 1018b.

Figure 10C:
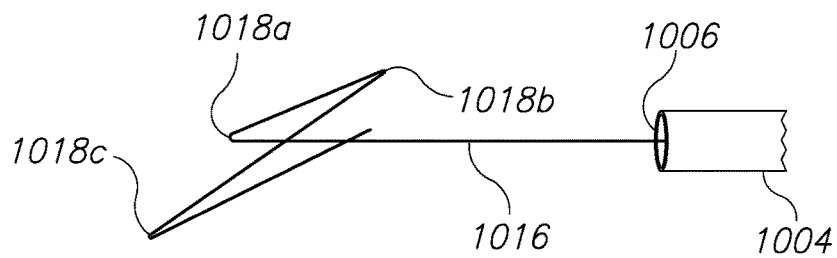

In FIG. 10c, grinder 1016 is an elastic rod, string or wire including three kinks, kinks 1018a, 1018b and 1018c.

Figure 10D:
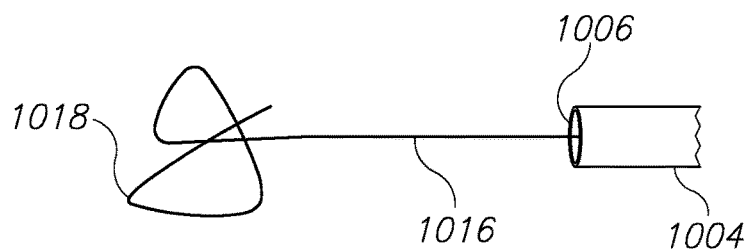

In FIG. 10d, grinder 1016 is an elastic rod, string or wire including more than three kinks generating a three-dimensional structure 1018.

Figure 10E:
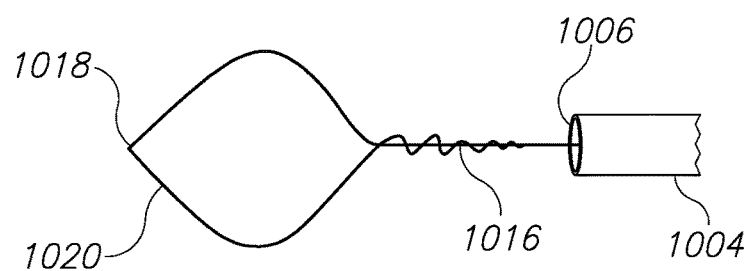

In FIG. 10e, grinder 1016 is an elastic rod, string or wire, which bends back to form a loop 1020. Loop 1020. Optionally, loop 1020 may include a kink 1018 at a distal end thereof.

Figure 10F:
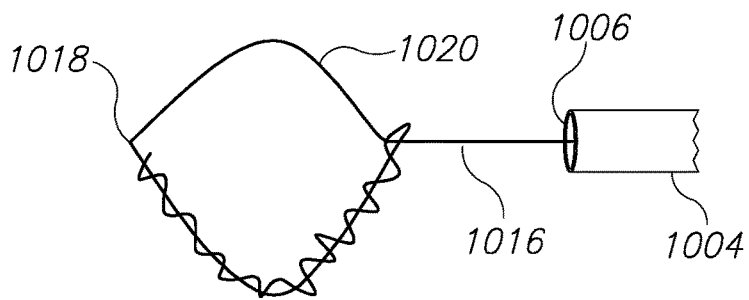

In FIG. 10f, grinder 1016 is an elastic rod, string or wire, which bends back to form a loop 1020 in which the wire is further looped around itself. Optionally, loop 1020 may include a kink (not shown) at a distal end thereof.

Figure 10G:
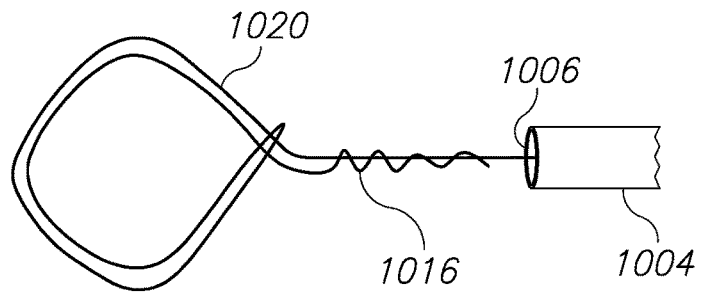

In FIG. 10g, grinder 1016 is an elastic rod, string or wire, which bends back to form a double loop 1020. Optionally, loop 1020 may include a kink 1018 at a distal end thereof.

Figure 10H:
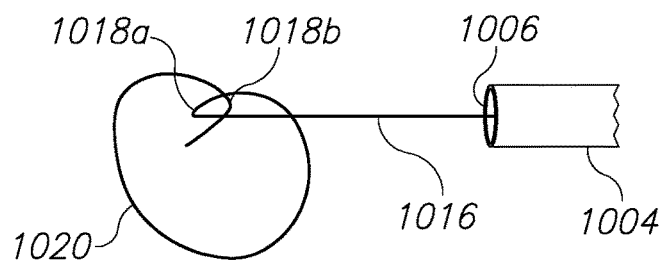
Figure 10I:
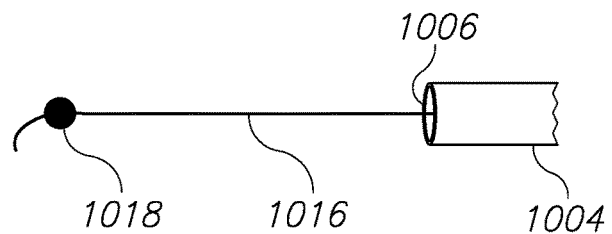

In FIG. 10h, grinder 1016 is an elastic rod, string or wire, which bends back to form a loop 1020. Loop 1020 is here formed by interweaving/knotting kinks 1018a and 1018b In FIG. 10i, grinder 1016 is an elastic rod, string or wire, which includes at least one knot or knob, here illustrated as knob 1018. Knob 1018 increases the weight of the distal end of grinder 1016, thereby augmenting the grinding function thereof, as essential described herein.

Reference is now made to FIG. 11a-FIG. 11e, which schematically illustrate protruding portions 1104 of a hollow shaft with at least two grinders, here grinders 1116a and 1116b extending from opening 1106, according to some embodiments. Grinder 1116 may include various structures and/or configurations as further illustrated hereinbelow. The structures exemplified below are illustrative only and additional configurations/structures are also applicable and thus within the scope of this disclosure. According to some embodiments, the structure/configuration may be pre-formed. Alternatively, the structure/configuration may be generated/activated once grinders 1116a and 1116b reach the designated treatment area. Grinder 1116 is here illustrated as being external to protruding section 1104; however other configurations in which grinder 1116 is located entirely, mostly or partially within protruding section 1104 are also envisaged and as such within the scope of the present disclosure.

Figure 11A:
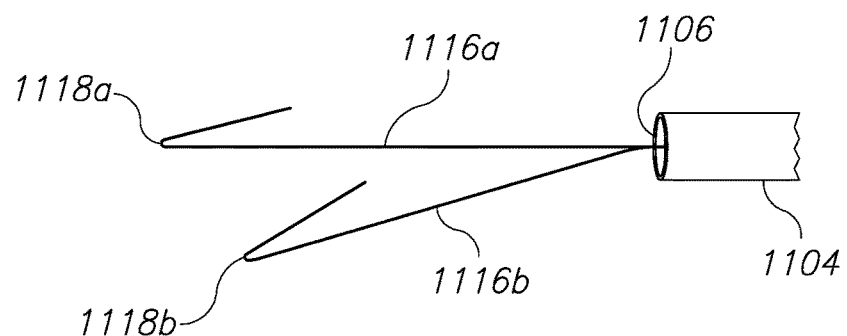
FIG. 11a-FIG. 11e schematically illustrate a protruding portion of a hollow shaft with a plurality of grinders extending from a distal opening thereof, according to some embodiments.

In FIG. 11a, protruding portions 1104 includes two grinders 1116a and 1116b comprising an elastic rod, string or wire. Grinders 1116a and 1116b each include a kink 1118a and 1118b generating hook structures. According to this embodiment, grinders 1116a and 1116b are separate non-intertwining structures.

Figure 11B:
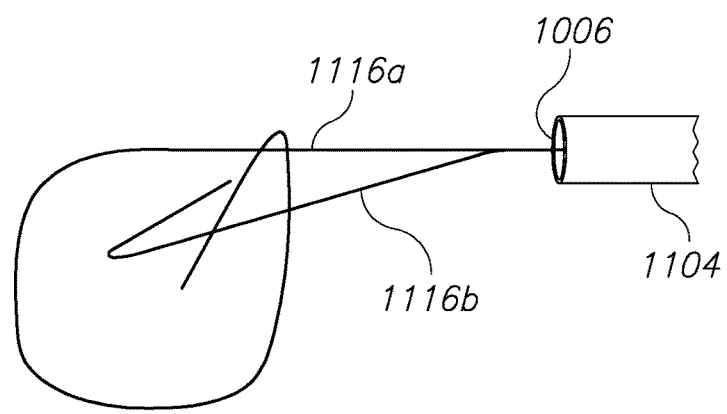

In FIG. 11b, protruding portions 1104 includes two grinders 1116a and 1116b comprising an elastic rod, string or wire. According to this embodiment, grinders 1116a form an interwoven three-dimensional structure.

Figure 11C:
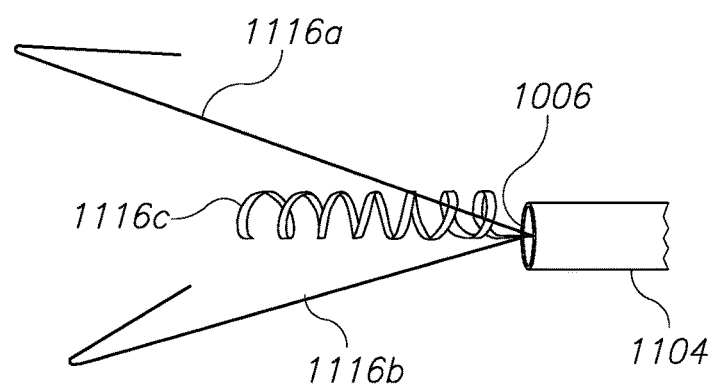

In FIG. 11c, protruding portions 1104 includes two grinders 1116a and 1116b, which are elastic rods, strings or wires and an additional grinder 1116c in the form of an Archimedes screw. According to this embodiment, grinders 1116a, 1116b and 1116c are separate non-intertwining structures.

Figure 11D:
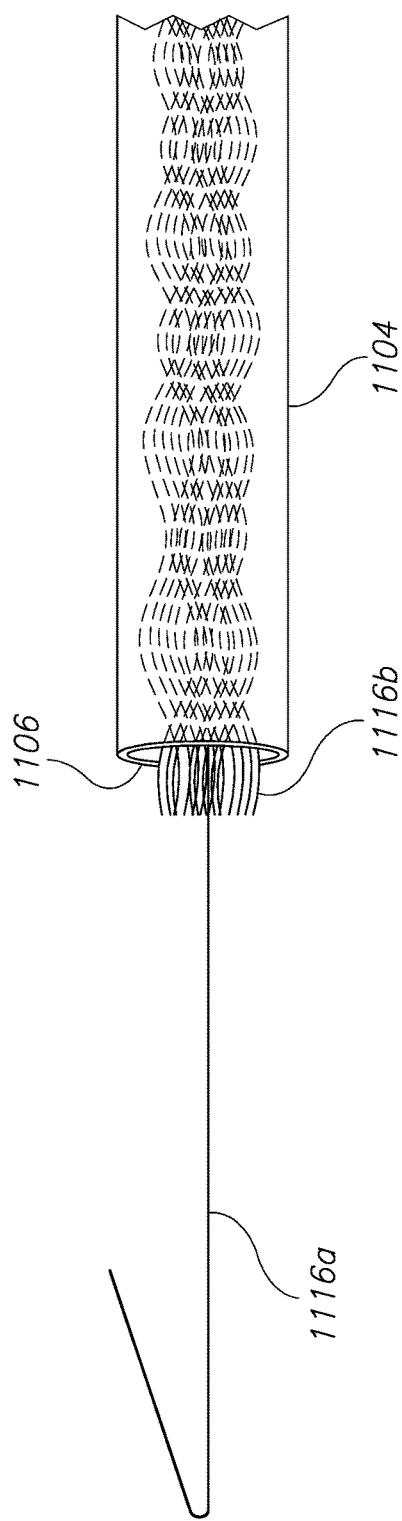

In FIG. 11d, protruding portions 1104 includes two sequentially connected grinders 1116a and 1116b. Grinder 1116a has a form of an elastic rod, string or wire, and grinder 1116b has a form of a cable, such as a cable made of at least two wires or strands, which are twisted or braided together.

Figure 11E:
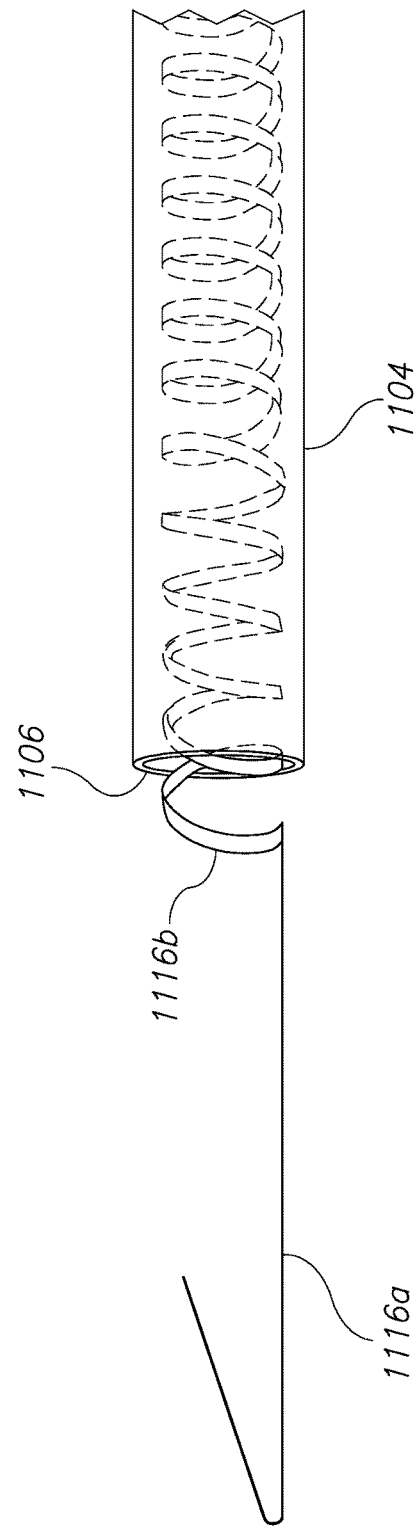

In FIG. 11e, protruding portions 1104 includes two sequentially connected grinders 1116a and 1116b. Grinder 1116a has a form of an elastic rod, string or wire, and grinder 1116b has a form of a Archimedes screw.

Figure 12:
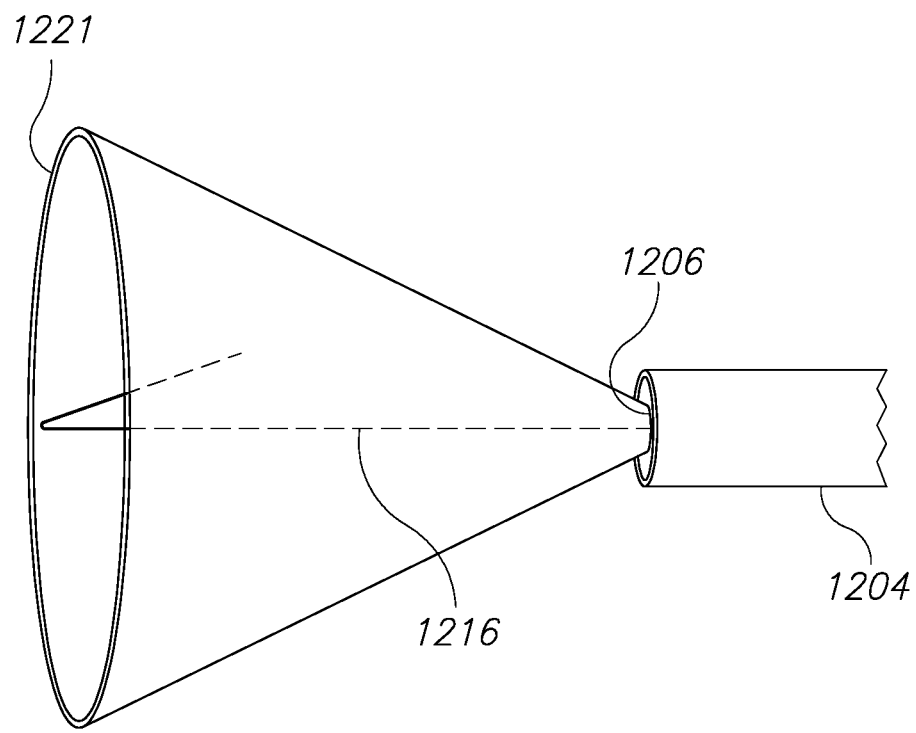
FIG. 12 schematically illustrate a protruding portion of a hollow shaft with a grinder extending from a distal opening thereof and an entrapping element, according to some embodiments.

Reference is now made to FIG. 12, which schematically illustrates protruding portions 1204 of a hollow shaft with a grinder 1216 extending from opening 1206, according to some embodiments. Grinder 1216 is here illustrated as an elastic rod, string or wire with a kink but other configurations of grinders, such as, but not limited to, those illustrated above may also be utilized and are within the scope of the present disclosure. Protruding portion 1204 further includes an entrapping element, here illustrated in the form of a cone 1221. Cone 1221 is configured to accommodate the shape of the sinus cavity, to direct grinded material towards the sinus ostium during operation and/or to protect the walls of the sinus cavity from damage caused by grinding wire 1216.

Figure 13:
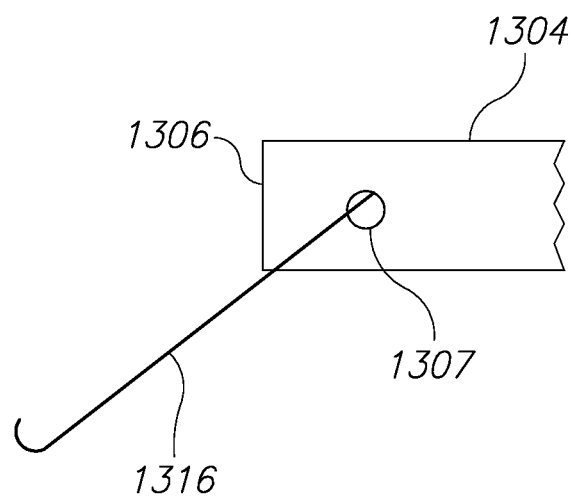
FIG. 13 schematically illustrate a protruding portion of a hollow shaft with a grinder extending from an aperture in the sidewall of the protruding portion, according to some embodiments.

Reference is now made to FIG. 13, which schematically illustrates protruding portions 1304 of a hollow shaft with a grinder 1316 extending from an aperture 1307, according to some embodiments. Grinder 1316 is here illustrated as an elastic rod, string or wire with a kink but other configurations of grinders, such as, but not limited to, those illustrated above may also be utilized and are within the scope of the present disclosure. Distal end 1306 of protruding portion 1304 may be sealed for example with an atraumatic tip, as essentially described herein. Additionally or alternatively, distal end 1306 may include a guide wire, a lens, a light source, a camera or any other suitable element, as essentially described herein. Aperture 1307 ensures that the flexible grinding wire exits protruding portion 1304 while posing minimal risk to surrounding tissues, such as the eye when inserted into a maxillary sinus cavity.

Figure 14:
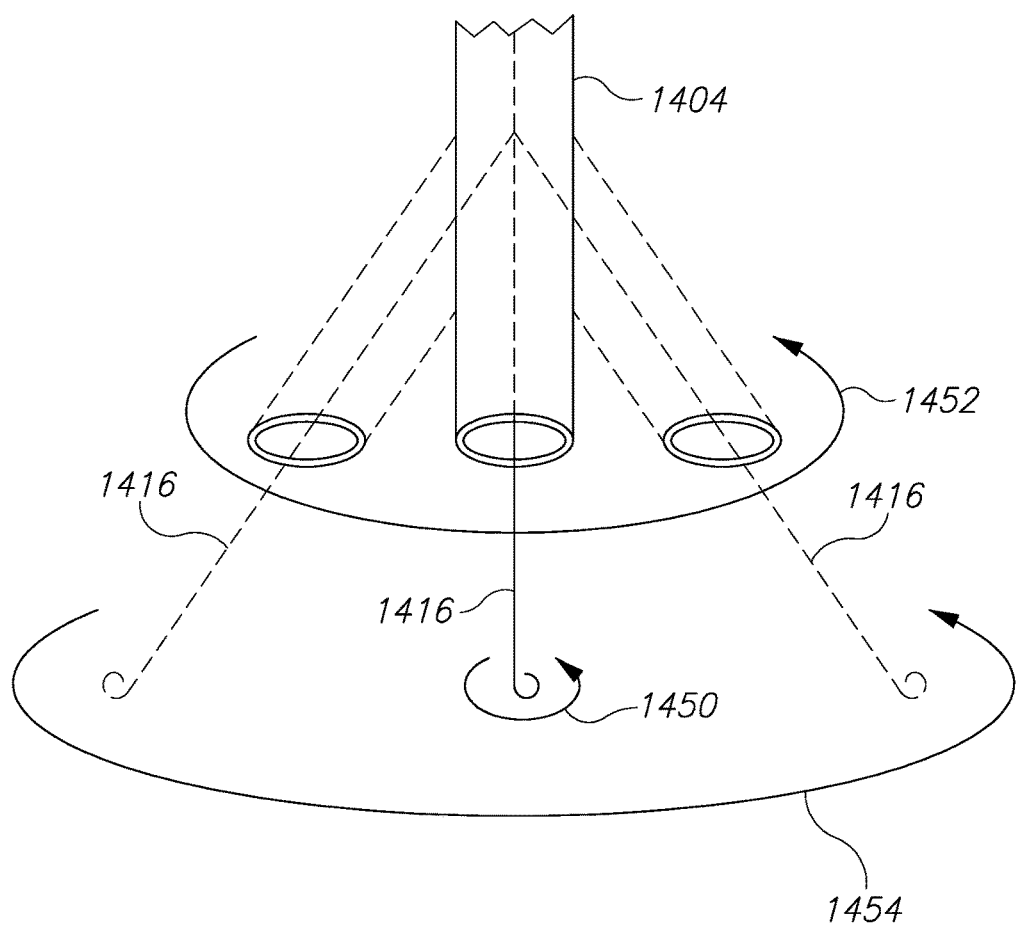
FIG. 14 schematically illustrates the rotation and precession of a cannula and its associated grinder, according to some embodiments.

Reference is now made to FIG. 14, which schematically illustrates rotation and precession of a cannula 1404 and its associated grinder 1416, according to some embodiments. Activation of the medical device (not shown) causes rotation of grinding wire 1416 within cannula 1404, as illustrated by arrow 1450 and induces precession of wire 1416 and cannula 1404, as illustrated by arrows 1452 and 1454. The combined rotational forces ensure efficient stirring of liquids and sheering and/or grinding of material present in the sinus cavity (not shown) and/or within inside cannula 1404.

Figure 15:
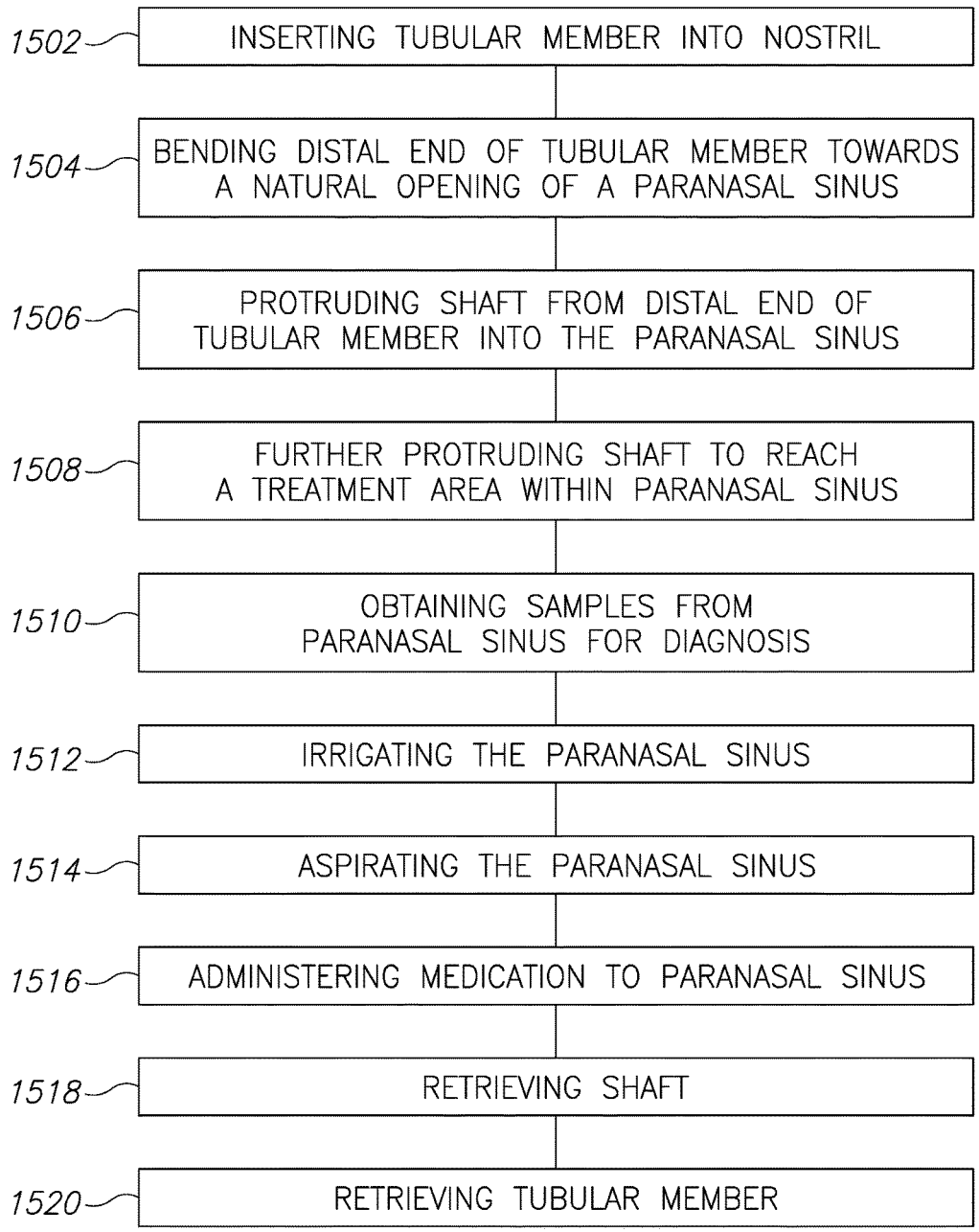
FIG. 15 schematically illustrates a method for treating a paranasal sinus condition, according to some embodiments.

Reference is now made to FIG. 15, which schematically illustrates a method 1500 for treating a paranasal sinus condition, according to some embodiments. The illustrated method begins by: inserting a tubular member into nostril (step 1502), bending a distal end of a tubular member towards a natural opening of a paranasal sinus (step 1504), extending a shaft, positioned within the tubular member, through the ostium of the paranasal sinus (step 1506), further extending the shaft to reach a treatment area within the paranasal sinus (step 1508). The method may then further include optional diagnosing and/or treatment steps, such as taking samples from the paranasal sinus for diagnosis (step 1510), irrigating the paranasal sinus (step 1512), aspirating the paranasal sinus (step 1514), and/or administering pharmaceutical composition/medication to paranasal sinus (step 1516). Upon finalization of the treatment, the shaft may be retrieved back into the tubular member (step 1518) whereafter the tubular member may be withdrawn from the nostril (step 1520).

Figure 16:
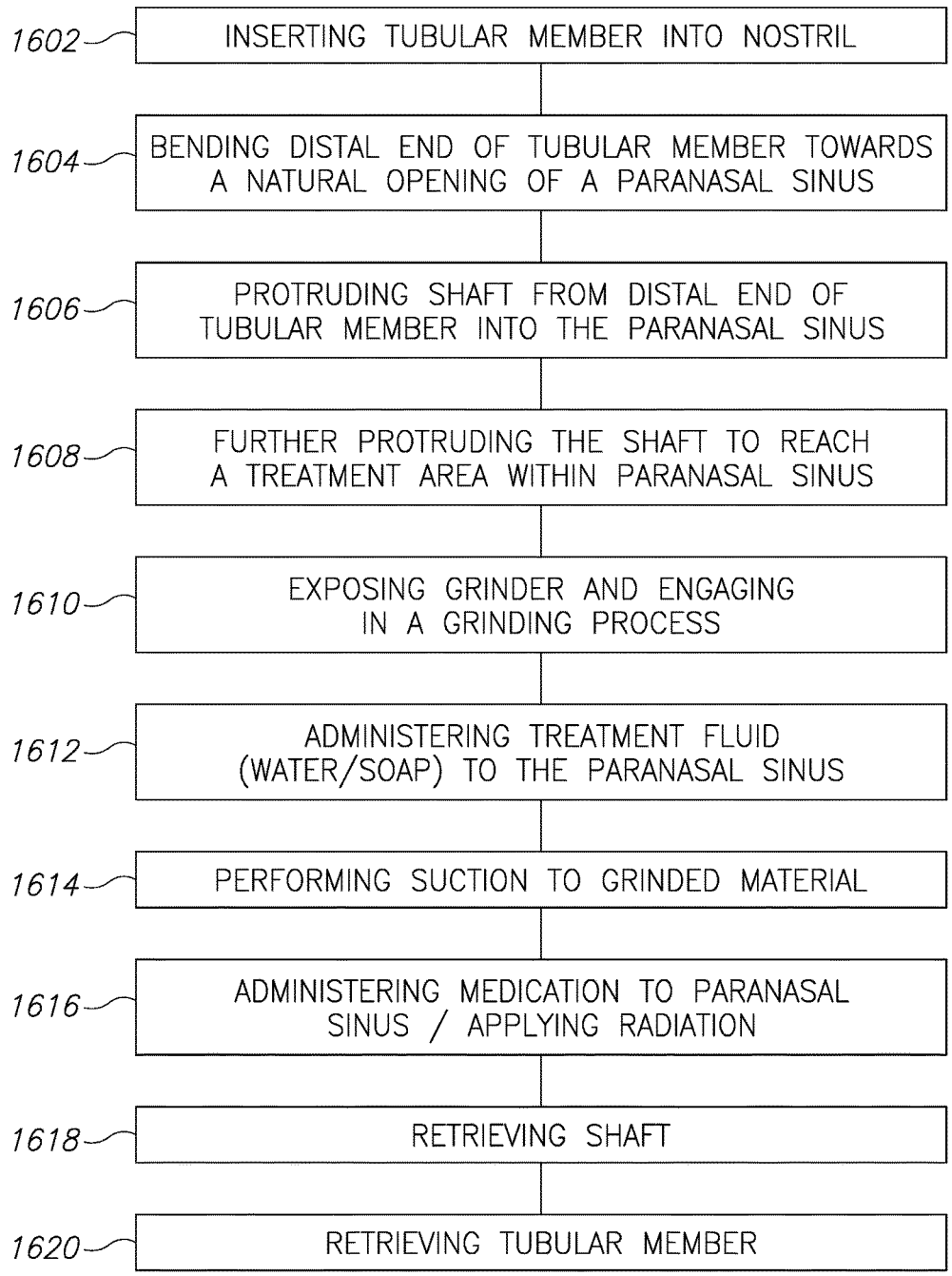
FIG. 16 schematically illustrates a method for treating a paranasal sinus condition with grinding, according to some embodiments.

Reference is now made to FIG. 16, which schematically illustrates a method 1600 for treating a paranasal sinus condition, according to some embodiments. The illustrated method begins by: inserting a tubular member into nostril (step 1602), bending a distal end of a tubular member towards a natural opening of a paranasal sinus (step 1604), protruding a shaft, positioned within the tubular member, through the ostium of the paranasal sinus (step 1606), further protruding shaft to reach a treatment area within paranasal sinus (step 1608). A grinder may then be exposed from the shaft followed by grinding of undesired material present in the sinus cavity (step 1610). Optionally the grinding process may be performed in conjunction with administration of a treatment fluid (water/soap) to the paranasal sinus (step 1612). During and/or upon completion of the grinding, suction of the grinded material may be performed (step 1614), optionally followed by administration of a medication to the paranasal sinus (step 1616). Upon finalization of the treatment, the shaft may be retrieved back into the tubular member (step 1618) and the tubular member may be withdrawn from the nostril (step 1620).

According to some embodiments, the hollow shaft is designed for penetrating into a paranasal sinus via the natural opening thereof without a guiding tubular member. According to some embodiments, the hollow shaft can have sinus seeker shape such as maxillary sinus seeker, frontal sinus seeker, sphenoid sinus seeker. According to some embodiments the hollow shaft can be inserted into the sinus ostium as a sinus seeker.

According to some embodiments, the hollow shaft distal end can have a penetration facilitation element. The penetration facilitation element can be inserted into the sinus ostium, and the hollow shaft proximal part can be pushed after the penetration facilitation element into the sinus cavity. According to some embodiments, the direction and insertion of the penetration facilitation element into the sinus ostia can be done without guiding the tubular member.

According to some embodiments, the hollow shaft can be inserted into the sinus riding along a guide-wire.

According to some embodiments, the hollow shaft is designed for penetrating into a paranasal sinus via opening of the paranasal sinus after surgical ostial dilation. According to some embodiments, the hollow shaft is designed for penetrating into a paranasal sinus via opening of the paranasal sinus after ostial balloon dilation.

According to some embodiments, the hollow shaft is designed for penetrating into a paranasal sinus via sinus wall puncturing. According to some embodiments, the hollow shaft can have sinus trocar or a needle shape, such as maxillary sinus trocar, frontal sinus trocar, sphenoid sinus trocar. According to some embodiments, the hollow shaft can be inserted into the sinus wall as a sinus trocar.

According to some embodiments, suction of fluids from the paranasal sinus may be carried out within the hollow shaft, within the tubular member and/or outside the tubular member. According to some embodiments, suction of fluids from the paranasal sinus may be carried out from a nostril-plug.

There is provided, according to some embodiments, a medical instrument or device for treating paranasal sinus conditions. The instrument comprises a main tubular member with a distal end and an opening at the distal end. The distal end is configured to be engaged or inserted into a nasal cavity of a subject through a nostril of a patient. The instrument further comprises a hollow shaft, movably located within the tubular member and may be moved to extend or protrude from the distal end of the tubular member through the opening. According to some embodiments, the shaft is at least partially made from a super-elastic material with a relaxed shape that is adapted for penetrating a paranasal sinus via a natural opening of the paranasal sinus and also adapted for being positioned inside the paranasal sinus for treatment. According to some embodiments the shaft is designed to reach a treatment area inside the paranasal sinus and to enable aspiration and/or irrigation inside the paranasal sinus.

According to some embodiments, the shaft is shaped for passing through a natural opening of a paranasal sinus without interrupting or damaging the bone structure of the paranasal sinus or the natural opening thereof. According to some embodiments, aspiration and/or irrigation of the paranasal sinus may be carried out by utilizing the hollow shaft. Advantageously, utilizing the super-elastic hollow shaft enables treatment without tissue harming invasive procedures.

According to some embodiments, the super-elastic material is a material that has a relaxed shape. The shape of the material may be strained when stress is applied to the material, and relaxed back to its original relaxed shape upon release of the stress. The straining and relaxing of the super-elastic material may be repeatedly executed without resulting in major deformation to the original relaxed shape of the super-elastic material. According to some embodiments, the tubular member and the distal end thereof may act as straining agents for the super-elastic material of the hollow shaft. When the shaft is passed within the tubular member, it gets stressed by the inner walls and is strained to roughly obtain the shape of the tubular member. When the super-elastic material of the shaft is extended from the distal end of the tubular member, the portion that has extended is no longer strained by the inner walls of the tubular member, and relaxes back to the relaxed shape.

According to some embodiments, the hollow shaft has a protruding portion, and a non-protruding portion. The protruding portion is configured to be inserted to a paranasal sinus through a natural opening of the paranasal sinus, and the non-protruding portion is configured to provide structural support to the protruding portion.

According to some embodiments, the relaxed shape of the super-elastic material is designed to position the shaft's distal end in or facing a treatment area inside the paranasal sinus. In some embodiments, the relaxed shape of the super-elastic material of the shaft is designed to reach the bottom of the paranasal sinus.

According to some embodiments, the super-elastic material comprises a pseudo-elastic metal-alloy with an $M_s$ and $A_f$ temperatures lower than 38° C. According to some embodiments, the super-elastic material comprises a pseudo-elastic metal-alloy with an $M_s$ and $A_f$ temperatures lower than 20° C. According to some embodiments, the super-elastic material comprises a pseudo-elastic metal-alloy with an $M_s$ and $A_f$ temperatures lower than 10° C., resulting in a pseudo-elastic metal-alloy that has super-elasticity properties when inserted inside a human body. According to some embodiments, the metal-alloy is a Nickle-Titanium Alloy. Each possibility represents as separate embodiment of the present invention. According to some embodiments, insertion of irrigation liquids changes the temperature of the water and causes a change of the super-elastic material shape.

According to some embodiments, the super elastic material comprises a pseudo-elastic alloy or a combination of pseudo-elastic alloys from the following: Ag—Cd, Au—Cd, Cu—Al—Ni, Cu—Sn, Cu—Zn, Cu—Zn—X, Fe—Pt, Mn—Cu, Fe—Mn—Si, Pt alloys, Co—Ni—Al, Co—Ni—Ga, Ni—Fe—Ga, Ti—Pd, Ni—Ti, Ni—Ti—Nb, Ni—Mn—Ga. Each possibility represents as separate embodiment of the present invention. According to some embodiments, the shaft or a super-elastic material thereof may be coated with a coating material.

According to some embodiments, the hollow shaft is configured to enable aspiration of the paranasal sinus. According to some embodiments, the hollow shaft is configured to enable irrigation of the paranasal sinus.

According to some embodiments, the medical device comprises a container. According to some embodiments, the contained is a medication container configured to contain medication to be delivered to the paranasal sinus. According to some embodiments, the container is a sample container configured to contain samples obtained from the paranasal sinus. According to some embodiments, the container is configured to contain both medication to be delivered to the paranasal sinus and samples taken from within the paranasal sinus. According to some embodiments, the container is configured to first contain medication to be delivered to the paranasal sinus, and then to contain samples obtained from within the paranasal sinus.

According to some embodiments, the medical device comprises a receptacle configured to receive a cartridge. According to some embodiments, the cartridge is a medication cartridge configured to contain medication to be delivered to the paranasal sinus. According to some embodiments, the cartridge is a sample cartridge configured to contain samples obtained from the paranasal sinus. According to some embodiments, the cartridge is configured to initially contain medication to be delivered to the paranasal sinus, and then to contain samples obtained from within the paranasal sinus.

According to some embodiments, the medical device includes an actuator, the actuator is configured to move the hollow shaft within the tubular member and to extend a protruding portion of the hollow shaft from the distal end of the tubular member. According to some embodiments, the actuator is an axially rotating wheel exposed for use at one side, and in contact with the hollow shaft at another side.

According to some embodiments, an illumination element is introduced. The illumination element may be inserted into the paranasal sinus through the hollow shaft. According to some embodiments, an illumination element is an optic fiber.

According to some embodiments, the medical device includes an orifice configured to enable insertion of an illumination element to the paranasal sinus via the hollow shaft.

According to some embodiments, the medical device includes an orifice configured to be mechanically connected to a liquid pump for providing liquids to the paranasal sinus via the hollow shaft. According to some embodiments, the pump may be a syringe such as but not limited to a safety syringe or a one hand operated syringe.

According to some embodiments, the medical device includes an orifice configured to be mechanically connected to a suction pump for retrieving samples and/or mucus and/or residues from the paranasal sinus via the hollow shaft.

According to some embodiments, the medical device is mobile. According to some embodiments, the medical device is handheld. In some embodiments, the medical device is powered by a mobile power source. In some embodiments, the medical device is powered by AC power source, such as an AC battery. According to some embodiments, the medical device is driven by a handle that can be turned in a circular motion, such as but not limited to a crank. According some embodiments, the rotation and/or vibration of the grinding wire may be achieved through a piezoelectric element. According to some embodiments, the medical device may be battery driven. According to some embodiments, the medical device may be portable. According to some embodiments, the device may have a total weight of less than 1.5 kg, less than 1 kg, less than 750 gram, less than 500 grams, less than 300 grams or less than 250 grams. Each possibility is a separate embodiment.

According to some embodiments, the medical device or cartridge comprises a medication preparation mechanism for mixing the medication with a liquid to enable reconstitution of the medication, or dilution thereof, prior to the delivery of the composition.

As used herein, a "pharmaceutical composition", "medicament" and/or "medicine" refers to a preparation of a composition comprising one or more pharmaceutically active agents, suitable for administration to a patient via a paranasal sinus.

According to some embodiments, the pharmaceutical composition further comprises at least one pharmaceutical acceptable carrier. According to some embodiments, the pharmaceutical composition may further comprise one or more stabilizers.

According to some embodiments, the hollow shaft is configured to provide a fluid containing a therapeutically effective amount of the pharmaceutical composition to the paranasal sinus.

As used herein, the term "therapeutically effective amount" refers to a pharmaceutically acceptable amount of a pharmaceutical composition which prevents or ameliorates at least partially, the symptoms of a particular disease, for example infectious or malignant disease, in a living organism to whom it is administered over some period of time.

The term "pharmaceutically acceptable" as used herein means approved by a regulatory agency of the Federal or a state government or listed in the U. S. Pharmacopeia or other generally recognized pharmacopeia for use in animals and, more particularly, in humans.

According to some embodiments, the pharmaceutical composition is in a liquid form such as solution, emulsion or suspension. Each possibility represents a separate embodiment of the present invention.

The pharmaceutical compositions of the invention may be prepared in any manner well known in the pharmaceutical art.

Useful pharmaceutically acceptable carriers are well known in the art, and include, for example, lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. Other pharmaceutical carriers can be sterile liquids, such as water, alcohols (e.g., ethanol) and lipid carriers such as oils (including those of petroleum, animal, vegetable or synthetic origin, such as peanut oil, soybean oil, mineral oil, sesame oil and the like), phospholipids (e.g. lecithin), polyethylene glycols, glycerine, propylene glycol or other synthetic solvents. Each possibility represents as a separate embodiment of the present invention.

Pharmaceutical acceptable diluents include, but are not limited to, sterile water, phosphate saline, buffered saline, aqueous dextrose and glycerol solutions, and the like. Each possibility is a separate embodiment of the invention.

According to some embodiments, the at least one therapeutic agent is selected from the group consisting of a hormone, a steroid, anti-inflammatory agent, antibacterial agent, anti-neoplastic agent, pain relief agent, narcotics, anti-viral agent, anti-fungal agent, anti-angiogenic agent, siRNA, immuno-therapy related agent, growth-inhibitory agent, apoptotic agent, cytotoxic agent and chemotherapeutic agent. Each possibility is a separate embodiment of the invention.

According to some embodiments, the paranasal sinus condition is a bacterial, fungal, and/or viral infection.

According to some embodiments, at least one of the pharmaceutical compositions comprises a therapeutically effective amount of medication for treating one or more of the medical conditions stated hereinbefore.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A medical device for treating and/or diagnosing a paranasal sinus condition, said medical device comprising:
    a flexible hollow cannula configured to be at least partially inserted through an ostium into a sinus cavity of a subject, said flexible hollow cannula comprising a flexible grinding wire configured to rotate at a speed of at least 100 RPM along a longitudinal axis thereof and thereby grind, chop and/or stir material present in said sinus cavity and/or inside said hollow cannula, wherein said grinding wire is configured to at least partially protrude out of said flexible hollow cannula, and wherein said flexible grinding wire is configured to grind material within the flexible hollow cannula essentially along a length thereof; and
    an elongated tubular member configured to receive said flexible hollow cannula wherein said flexible hollow cannula is configured to retractably extend from a distal end of said elongated tubular member;
    wherein the rotation of said grinding wire within the hollow cannula is configured to induce precession of a distal end of said hollow cannula, and wherein the cannula is further configured to allow irrigation of the sinus cavity and/or suction therefrom, whereby intra-sinus turbulence of said irrigation is enhanced by the rotation of the grinding wire to thereby augment grinding, chopping and/or stirring of material present in said sinus cavity, essentially without harming the mucosa.

2. The medical device of claim 1, wherein said distal end of the elongated tubular member is bent or bendable so as to face the ostium of the paranasal sinus, once inserted into the subject's nose.

3. The medical device of claim 1, wherein the precession of said flexible grinding wire and/or of said hollow cannula, augments the grinding, chopping and/or stirring of said material, essentially without penetrating, removing or harming the sinus mucosa, while being in contact with the mucosa.

4. The medical device of claim 1, wherein said precession of said hollow cannula, is further configured to enlarge the ostium.

5. The medical device of claim 1, wherein said precession of said hollow cannula is configured to reduce intra-sinus pressure, or prevent pressure accumulation.

6. The medical device of claim 1, wherein said flexible hollow cannula is configured to penetrate through the ostium of the paranasal sinus, when said distal end of said elongated tubular member faces said ostium.

7. The medical device of claim 6, wherein said flexible hollow cannula comprises an external diameter of up to 2 mm and is configured to penetrate through said ostium without surgical dilation and/or without harming the mucosa or a sinus bone.

8. The medical device of claim 1, further comprising an actuator configured to extend and withdraw said flexible hollow cannula from and to said elongated tubular member.

9. The medical device from claim 8, wherein said flexible grinding wire is configured to propel grinded material and/or irrigation fluids towards the sinus ostium.

10. The medical device of claim 1, wherein said flexible grinding wire is configured to move back and forth along a longitudinal axis thereof and wherein said flexible grinding wire comprises a wire, a string a fiber, a spring, a coil, a screw, a cable, a tube or any combination thereof.

11. The medical device of claim 1, wherein said flexible grinding wire has at least along a section of a length thereof a shape of a spring, a coil or a screw, said shape is configured to propel grinded material and/or irrigation fluids within said cannula towards a proximal end of said cannula and/or to reduce blockages within said cannula.

12. The medical device of claim 1, wherein said flexible hollow cannula and/or said flexible grinding wire comprise a super-elastic material or pseudo-elastic material.

13. The medical device of claim 1, wherein said flexible grinding wire is configured to assume a predetermined shape once delivered through said flexible hollow cannula and inserted into the sinus cavity, wherein the predetermined shape comprising at least one curve, loop, knot and/or knob at a distal end thereof.

14. The medical device of claim 1, wherein said flexible grinding wire, once delivered through said flexible hollow cannula and inserted into the sinus cavity, is configured to assume a desired configuration and position by contacting the cavity inner walls.

15. The medical device of claim 1, wherein a distal end of said flexible hollow cannula comprises an atraumatic tip, a guide wire, a lens, a light source, a camera or any combination thereof.

16. The medical device of claim 1, wherein said flexible hollow cannula is configured to assume a predetermined configuration once inserted into the sinus cavity, and said flexible grinding wire is also configured to assume a predetermined shape once delivered through said flexible hollow cannula and inserted into the sinus cavity.

17. The medical device of claim 1, wherein said flexible grinding wire is configured to rotate at at least 1000 RPM.

18. The device of claim 1, wherein the grinding wire is configured to be rotated by a motor.

19. The device of claim 1, wherein said flexible hollow cannula precession movement apply pressure or displace the mucosa in a sinus ostia, without harming or displacing the sinus bone.

20. A method for treating and/or diagnosing a paranasal sinus condition, said medical device comprising:
  inserting, at least partially, a flexible hollow cannula through an ostium into a sinus cavity of a subject, the flexible hollow cannula comprising a flexible grinding wire, wherein the flexible hollow cannula is configured to retractably extend from a distal end of an elongated tubular member configured to receive said flexible hollow cannula wherein said flexible hollow cannula is configured to retractably extend from a distal end of said elongated tubular member, wherein said grinding wire is configured to at least partially protrude out of said flexible hollow cannula, and wherein said flexible grinding wire is configured to grind material within the flexible hollow cannula essentially along a length thereof;
  activating rotation of the grinding wire along a longitudinal axis thereof at a speed of at least 100 RPM, thereby grinding, chopping and/or stirring material present in the sinus cavity and/or inside said hollow cannula, wherein the rotation of said grinding wire within the hollow cannula is configured to induce precession of a distal end of said hollow cannula; and
  conducting irrigation and/or aspiration during the rotation of the grinding wire, wherein the grinding wire is configured to stir irrigation liquids and/or mucus materials thereby causing turbulence in the sinus cavity to thereby augment intra-sinus grinding, chopping and/or stirring of material present in the sinus cavity, whereby intra-sinus turbulence of said irrigation is enhanced by the rotation of the grinding wire to thereby augment grinding, chopping and/or stirring of material present in said sinus cavity, essentially without harming the mucosa.

21. A medical system for treating and/or diagnosing a paranasal sinus condition, said medical device comprising:
  a flexible hollow cannula configured to be at least partially inserted through an ostium into a sinus cavity of a subject, said flexible hollow cannula comprising a flexible grinding wire configured to rotate at a speed of at least 100 rpm along a longitudinal axis thereof and thereby grind, chop and/or stir material present in said sinus cavity and/or inside said hollow cannula, wherein said grinding wire is configured to at least partially protrude out of said flexible hollow cannula, and wherein said flexible grinding wire is configured to grind material within the flexible hollow cannula essentially along a length thereof;
  an elongated tubular member configured to receive said flexible hollow cannula, said flexible hollow cannula is configured to retractably extend from a distal end of said elongated tubular member; wherein said distal end being bent or bendable so as to face the ostium of the paranasal sinus, once inserted into the subject's nose; and
  a handle mechanically connected to the tubular member at a proximal end thereof, the handle is configured to control movement and extension of the hollow cannula, the handle comprises a pumping-orifice configured to provide fluid to the hollow cannula, and a suction-orifice configured to provide suction from the hollow cannula, wherein intra-sinus turbulence of said irrigation is enhanced by the rotation of the grinding wire to thereby augment grinding, chopping and/or stirring of material present in said sinus cavity essentially without harming the mucosa.

\* \* \* \* \*